US007244565B2

(12) United States Patent
Kasid et al.

(10) Patent No.: US 7,244,565 B2
(45) Date of Patent: Jul. 17, 2007

(54) GENE SHINC-3 AND DIAGNOSTIC AND THERAPEUTIC USES THEREOF

(75) Inventors: Usha Kasid, Rockville, MD (US); Isamu Sakabe, Arlington, VA (US); Imran Ahmad, Wadsworth, IL (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 10/411,930

(22) Filed: Apr. 10, 2003

(65) Prior Publication Data

US 2004/0005603 A1    Jan. 8, 2004

Related U.S. Application Data

(60) Provisional application No. 60/371,116, filed on Apr. 10, 2002.

(51) Int. Cl.
  *C07H 21/02*  (2006.01)
(52) U.S. Cl. .......................................... 435/6; 536/23.1
(58) Field of Classification Search .............. 536/23.1; 535/6; 514/44; 435/6
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,551,433 A | 11/1985 | DeBoer |
| 4,560,655 A | 12/1985 | Baker |
| 4,657,866 A | 4/1987 | Kumar |
| 4,745,051 A | 5/1988 | Smith et al. |
| 4,767,704 A | 8/1988 | Cleveland et al. |
| 4,777,127 A | 10/1988 | Suni et al. |
| 4,816,567 A | 3/1989 | Cabilly et al. |
| 4,837,148 A | 6/1989 | Cregg |
| 4,889,806 A | 12/1989 | Olson et al. |
| 4,927,762 A | 5/1990 | Darfler |
| 4,929,555 A | 5/1990 | Cregg et al. |
| 4,959,314 A | 9/1990 | Mark et al. |
| 5,013,830 A | 5/1991 | Ohtsuka et al. |
| 5,091,309 A | 2/1992 | Schlesinger et al. |
| 5,149,655 A | 9/1992 | McCabe et al. |
| 5,149,797 A | 9/1992 | Pederson et al. |
| 5,185,440 A | 2/1993 | Davis et al. |
| 5,206,152 A | 4/1993 | Sukhatme |
| 5,217,879 A | 6/1993 | Huang et al. |
| 5,219,740 A | 6/1993 | Miller et al. |
| 5,403,711 A | 4/1995 | Walder et al. |
| 5,422,120 A | 6/1995 | Kim |
| 5,491,133 A | 2/1996 | Walder et al. |
| 5,514,758 A | 5/1996 | Muller et al. |
| 5,530,101 A | 6/1996 | Queen et al. |
| 5,536,821 A | 7/1996 | Agrawal et al. |
| 5,541,306 A | 7/1996 | Agrawal et al. |
| 5,550,111 A | 8/1996 | Suhadolnik et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,580,859 A | 12/1996 | Felgner et al. |
| 5,585,089 A | 12/1996 | Queen et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,597,696 A | 1/1997 | Linn et al. |
| 5,610,018 A | 3/1997 | Di Fiore et al. |
| 5,625,050 A | 4/1997 | Beaton et al. |

(Continued)

FOREIGN PATENT DOCUMENTS

| | | |
|---|---|---|
| EP | 36776 A2 | 9/1981 |
| EP | 0 127 839 A2 | 12/1984 |
| EP | 0 155 476 A1 | 9/1985 |
| EP | 0 244 234 A2 | 11/1987 |

(Continued)

OTHER PUBLICATIONS

Riedel et al., "The Mitogenic Response of T Cells to Interleukin-2 Requires Raf-1", *Eur. J. Immunol.*, 23, 3146-3150 (1993).
Suy et al., "Nitroxides Tempol and Tempo Induce Divergent Signal Transduction Pathways in MDA-MB 231 Breast Cancer Cells", *J. Biol. Chem.*, 273, 17817-17878 (1998).

(Continued)

*Primary Examiner*—Shanon Foley
*Assistant Examiner*—Brandon Fetterolf
(74) *Attorney, Agent, or Firm*—DLA Piper US LLP

(57) ABSTRACT

The invention provides a SHINC-3 polynucleotide, which can be a nucleic acid encoding all or a portion of a SHINC-3 protein, or a complementary polynucleotide or antisense polynucleotide. In another aspect, the invention provides a SHINC-3 polypeptide, which can be a full-length SHINC-3 protein or a fragment thereof or an analog or homolog thereof. Desirably, the SHINC-3 polypeptide modulates apoptosis. In another aspect, the invention provides an antibody that specifically binds a SHINC-3 polypeptide.

In another aspect, the invention provides diagnostic methods. For example, the method affords a method for identifying compounds that modulate apoptosis. In another aspect, the invention provides a method for detecting or evaluating the prognosis of a cancer. In another aspect, the invention provides diagnostic compositions for detection of cancer.

In another aspect, the invention provides a method of modulating apoptosis or invention or preventing a cancer, tumor growth and/or metastasis by administration of an agent that modulates the expression and/or activity of SHINC-3.

In another aspect, the invention provides formulations of SHINC-3 polynucleotides or proteins. Preferably, such compositions will comprise liposomal formulations.

8 Claims, 13 Drawing Sheets

U.S. PATENT DOCUMENTS

| | | | |
|---|---|---|---|
| 5,641,670 | A | 6/1997 | Treco et al. |
| 5,652,355 | A | 7/1997 | Metelev et al. |
| 5,700,922 | A | 12/1997 | Cook |
| 5,776,745 | A | 7/1998 | Ketner et al. |
| 5,801,154 | A | 9/1998 | Baracchini et al. |
| 5,919,773 | A | 7/1999 | Monia et al. |
| 5,939,598 | A | 8/1999 | Kucherlapati et al. |
| 5,958,773 | A | 9/1999 | Monia et al. |
| 6,333,314 | B1 | 12/2001 | Kasid et al. |

FOREIGN PATENT DOCUMENTS

| | | |
|---|---|---|
| EP | 0 345 242 A2 | 12/1989 |
| EP | 0 415 731 A2 | 3/1991 |
| EP | 0 524 968 B1 | 2/1993 |
| EP | 1074617 A2 * | 2/2001 |
| GB | 2 200 651 A | 8/1988 |
| WO | WO 87/00195 A1 | 1/1987 |
| WO | WO 90/03430 A1 | 4/1990 |
| WO | WO 90/07936 A1 | 7/1990 |
| WO | WO 90/11092 A1 | 10/1990 |
| WO | WO 91/00357 A1 | 1/1991 |
| WO | WO 91/02805 A2 | 3/1991 |
| WO | WO 91/10741 A1 | 7/1991 |
| WO | WO 91/14445 A1 | 10/1991 |
| WO | WO 92/05266 A2 | 4/1992 |
| WO | WO 92/10578 A1 | 6/1992 |
| WO | WO 92/11033 A1 | 7/1992 |
| WO | WO 93/03769 A1 | 3/1993 |
| WO | WO 93/04170 | 3/1993 |
| WO | WO 93/06248 | 4/1993 |
| WO | WO 93/09239 A1 | 5/1993 |
| WO | WO 93/10218 A1 | 5/1993 |
| WO | WO 93/11230 A1 | 6/1993 |
| WO | WO 93/19191 A1 | 9/1993 |
| WO | WO 93/25234 A1 | 12/1993 |
| WO | WO 93/25698 A1 | 12/1993 |
| WO | WO 94/02602 A1 | 2/1994 |
| WO | WO 94/03622 A1 | 2/1994 |
| WO | WO 94/12649 A2 | 6/1994 |
| WO | WO 94/15645 | 7/1994 |
| WO | WO 94/21792 A2 | 9/1994 |
| WO | WO 94/23697 A1 | 10/1994 |
| WO | WO 94/28938 A1 | 12/1994 |
| WO | WO 95/00655 A1 | 1/1995 |
| WO | WO 95/07994 A2 | 3/1995 |
| WO | WO 95/11984 A2 | 5/1995 |
| WO | WO 95/13796 A1 | 5/1995 |
| WO | WO 95/27044 A1 | 10/1995 |
| WO | WO 95/27069 A1 | 10/1995 |
| WO | WO 95/30763 A2 | 11/1995 |
| WO | WO 96/30498 A1 | 10/1996 |
| WO | WO 96/33735 A1 | 10/1996 |
| WO | WO 96/34096 A1 | 10/1996 |
| WO | WO 98/24893 A2 | 6/1998 |
| WO | WO 00/00157 | 1/2000 |
| WO | WO 02/059337 A1 | 8/2002 |
| WO | WO 02/081639 A2 | 10/2002 |
| WO | WO 02/081640 A2 | 10/2002 |
| WO | WO 02/081641 A2 | 10/2002 |
| WO | WO 02/081642 A2 | 10/2002 |

OTHER PUBLICATIONS

Tornkvist et al., "Inhibition of Raf-1 Kinase Expression Abolishes Insulin Stimulation of DNA Synthesis in H4IIE Hepatoma Cells", *J. Biol. Chem.*, 269, 13919-13921 (1994).

Bruder et al., "Serum-, TPA-, and Ras-induced expression from AP-1/Ets-driven promoters requires Raf-1 kinase," *Genes & Dev.*, 6, 545-556 (1992).

Bruhn et al., "Isolation and characterization of human cDNA clones encoding a high mobility group box protein that recognizes structural distions to DNA caused by binding of the anticancer agent cisplatin," *Proc. Natl. Acad. Sci. USA*, 89, 2307-2311 (1992).

Cozens et al., "DNA sequences of two expressed nuclear genes for human mitochondrial ADP\ATP translocase," *J. Mol. Biol.*, 206, 261-280 (1989).

Davis, "The many faces of epidermal growth factor repeats," *New Biol.*, 22, 410-419 (1990).

Dent et al. "Activation of mitogen-activated protein kinase kinase by v-Raf in NIH3T3 cells and in vitro," *Science*, 257, 1404-1407 (1992).

Devary et al., "The mammalian ultraviolet response is triggered by activation of Src tyrosine kinases," *Cell*, 71, 1081-1091 (1992).

Dinchuk et al., "Aspartyl â-hydroxylase (Asph) and an evolutionarily conserved isoform of asph missing the catalytic domain share exons with junctin," *J. Biol. Chem.*, 275, 39543-39554 (2000).

Downing et al., "Solution structure of a pair of calcium-binding epidermal growth factor-like domains: implications for the Marfan syndrome and other genetic disorder," *Cell*, 85, 597-605 (1996).

Fiermonte et al, "Identification of the human mitochondrial oxodicarboxylate carrier," *J. Biol. Chem.*, 276, 8225-8230 (2001).

Finco et al., "κB site-dependent induction of gene expression by diverse inducers of nuclear factor κB requires Raf-1," *J. Biol. Chem.*, 268, 17676-17679 (1993).

Gokhale et al., "Antisense *raf* Oligodexyribonucleotide is protected by liposomal encapsulation and inhibits Raf-1 protein expression in vitro and in vivo: Implication for gene therapy of radioresistant cancer," *Gene Therapy*, 4, 1289-1299 (1997).

Green et al., "Mitochondria and Apoptosis," *Science*, 281, 1309-1312 (1998).

Goruppi et al., "The product of a gas6 splice variant allows the release of the domain responsible for Axl tyrosine kinase receptor activation," *FEBS Lett.*, 415, 59-63 (1997).

Heidecker et al., "Mutational activation of c-*raf*-1 and definition of the minimal transforming sequence," *Mol. Cell. Biol.*, 10, 2503-2512 (1990).

Heidecker et al., "The role of Raf-1 phosphorylation in signal transduction," *Adv. Cancer Res.*, 58, 53-73 (1992).

Houldworth et al., "Two distinct genes for ADP\ATP translocase are expressed at the mRNA level in adult human liver," *Proc. Natl. Acad. Sci. U.S.A.*, 85, 377-381 (1988).

Howe et al., "Activation of the MAP kinase pathway by the protein kinase Raf," *Cell*, 71, 335-342 (1992).

Kasid et al., "The *raf* oncogene is associated with a radiation-resistant human laryngeal cancer," *Science*, 237, 1039-1041 (1987).

Kasid et al., "Effect of antisense c-raf-1 on tumorigenicity and radiation sensitivity of a human squamous carcinoma," *Science*, 243, 1354-1356 (1989).

Kasid et al., "Oncogenic basis of radiation resistance," *Avd. Cancer Res.*, 61, 195-233 (1993).

Kasid et al., "Activation of Raf by ionizing radiation," *Nature*, 382, 813-816 (1996).

Kelson et al., "Human liver fatty aldehyde dehydrogenase: Microsomal localization, purification, and biochemical characterization," *Biochim. Biophys. Acta.*, 1335, 99-110 (1997).

Kolarov et al., "A third ADP\ATP translocator gene in yeast," *J. Biol. Chem.*, 265, 12711-12716 (1990).

Kolch et al., "Raf-1 protein kinase is required for growth of induced NIH3T3 cells," *Nature*, 349, 426-428 (1991).

Korioth et al., "Cloning and characterization of the human gene encoding aspartly beta-hydroxylase," *Gene*,150, 395-399 (1994).

Kyriakis et al., "Raf-1 activiates MAP kinase-kinase," *Nature*, 358, 417-421 (1992).

Lawson et al., "Separate genes encode functionally equivalent ADP\ATP carrier proteins in *Saccharomyces cerevisiae*. Isolation and analysis of AAC2," *J. Biol. Chem.*, 263, 14812-14818 (1988).

Lim et al., "cDNA cloning and characterization of human cardiac junctin," *Gene*, 255, 35-42 (2000).

Luciakova et al., "In vivo mapping of the human adenine nucleotide translocator-2 (ANT2) promoter provides support for regulation by a pair of proximal Sp-1-activating sites and an upstream silencer element," *Biochem. J.*, 352, 519-523 (2000).

Marshall et al., "Specificity of receptor tyrosine kinase signaling: transient versus sustained extracellular signal-regulated kinase activation," *Cell*, 80, 179-185 (1995).

Marzo et al., "The permeability transition pore complex: a target for apoptosis regulation by caspases and bcl-2-related proteins," *J. Exp. Med.*, 187, 1261-1271 (1998).

Monia et al., "Antitumor activity of a phosphorothioate antisense oligodeozynucleotide targeted against c-raf kinase," *Nature Med.*, 2, 668-675 (1996).

Nakamura et al., "A novel secreted RGD protein expressed in developing, atherosclcerotic, and balloon-injured arteries," *J. Biol. Chem.*, 274, 22476-22483 (1999).

Neckelmann et al., "cDNA sequence of a human skeletal muscle ADP\ATP translocator: lack of a leader peptide. Divergence from a fibroblast translocator cDNA, and coevolution with miochondrial DNA genes," *Proc. Natl. Acad. Sci. USA*, 84, 7580-7584 (1987).

Patel et al., "Constitutive activation of Raf-1 correlates with morphological transformation and abrogation of tyrosine phosphorylation of distinct sets of proteins in human squamous carcinoma cells," *Mol. Carcinog.*, 18, 1-6 (1997).

Patel et al., "Constitutive modulation of Raf-1 protein kinase is associated with differential gene expression of several known and unknown genes," *Mol. Med.*, 3, 674-685 (1997).

Patel et al., "Identification of seven differentially displayed transcripts in human primary and matched metastatic head and neck squamous carcinoma cell lines: Implications in metastasis and/or radiation response," *Eur. J. Cancer B. Oral Oncol.*, 33, 197-203 (1997).

Pfeifer at al., "Effects of c-*raf*-1 and c-*myc* expression on radiation response in an in vitro model of human small-cell-lung-carcinoma," *Biochem. Biophy. Res. Commun.*, 252, 481-486 (1998).

Pferifer et al., "Cooperation of c-*raf*-1 and c-*myc* protooncogenes in the neoplastic transformation of simian virus 40 large tumor antigen-immortalized human bronchial epithelial cells," *Proc. Natl. Acad. Sci. USA*, 86, 10075-10079 (1989).

Qureshi et al., "An inhibitory mutant of c-Raf-1 blocks v-Src-induced activation of the Egr-1 promoter," *J. Biol. Chem.*, 266, 20594-20597 (1991).

Rapp, "Role of Raf-1 serine/threonine protein kinase in growth factor signal transduction," *Oncogene*, 6, 495-500 (1991).

Rebay et al., "Specific EGF repeats of Notch mediate interactions with Delta and Serrate: implications for Notch as a multifunctional receptor," *Cell*, 67, 687-699 (1991).

Rees et al., "The role of beta-hydroxyaspartate and adjacent carboxylate residues in the first EGF domain of human factor IX," *EMBO J.*, 7, 2053-2061 (1988).

Rogers et al., "Genomic organization and expression of the human fatty aldehyde dehydrogenase gene (FALDH)," *Genomics*, 39, 127-135 (1997).

Shengfeng et al., "Raf-1 protein kinase activates the NF-κB transcription factor by dissociating the cytoplamic NFκ-IκB complex," *Proc. Natl. Acad. Sci. USA*,90, 9247-9251 (1993).

Soldatenkov et al., "Inhibition of Raf-1 protein kinase by antisense phosphorothioate oligodeoxyribonucleotide is associated with sensitization of human laryngeal squamous carcinoma cells to gamma radiation," *Cancer J. Sci. Am.*, 3, 13-20 (1997).

Stanton et al., "Definition of the human *raf* amino-terminal regulatory region by deletion mutagenesis," *Oncogene*, 15, 53-61 (1989).

Stenflo, "Structure-function relationships of epidermal growth factors modules in vitamin K-dependent clotting factor," *Blood*, 78. 1637-1651 (1991).

Sun et al., "Identification of a protein isolated from senescent human cells that binds to hepatitis B virus X antigen," *Hepatology*, 27, 228-239 (1998).

Sunnerhagen et al., "The effect of aspartate hydroxylation on calcium binding to epidermal growth factor-like modules in coagulation factors IX and X," *J. Biol. Chem.*, 268, 2339-2344 (1993).

Suy et al., "Association of Grb2 with Sos and Ras with Raf-1 upon gamma irradiation of breast cancer cells," *Oncogene*, 15, 53-61 (1997).

Troppmair et al., "V-Raf/f-Myc synergism in abrogation of IL-3 dependence: v-Raf suppresses apoptosis," *Curr. Top. Microbiol. Immunol.*, 182, 453-460 (1992).

Wang et al., "Bcl-2 targets the protein kinase Raf-1 to mitochondria," *Cell*, 87, 629-638 (1996).

Liang et al., *Science*, 257, 967-971 (Aug. 14, 1992).

Gokhale et al., *Antisense Nucleic Acid Drug Dev.*, 9, 191-201 (1999).

Muzio et al., *Cell*, 85(6), 817-827 (1996).

Nakai et al., *Genomics*, 14, 897-911 (1992).

Nicoletti et al., *Journal of Immunological Methods*, 139(2), 271-279 (1991).

Oda et al., *Biochemical and Biophysical Research Communications*, 193(3), 897-904 (1993).

Ohmichi et al., *The Journal of Biological Chemistry*, 267(21), 14604-14610 (1992).

Ostade et al., *Nature*, 361 (6409), 266-269 (1993).

Padlan et al., *Molecular Immunology*, 28(4/5), 489-498 (1991).

Padlan et al., *Molecular Immunology*, 31(3), 169-217 (1994).

Patel et al., *ACTA Oncological*, 37(5), 475-478 (1998).

Philip, *Molecular and Cellular Biology*, 14(4), 2411-2418 (1994).

Pinckard et al., *Clinical and Experimental Immunology*, 2, 331-340 (1967).

Prasad et al., *Molecular and Cellular Biology*, 12(11), 5260-5267 (1992).

Pulverer et al., *Nature*, 353(6345), 670 (1991).

Ram et al., *Cancer Research*, 53(1), 83-88 (1993).

Rapp et al, *The Oncogene Handbook*, (Elsevier Science Publishers, New York), 213-253 (1988).

Robbins et al., *Diabetes*, 36(7), 838-845 (1987).

Roggenkamp et al., *Molecular & General Genetics*, 202(2), 302-308 (1986).

Rosenfeld et al., *Science*, 252(5004), 431-434 (1991).

Sacchi et al., *Archives of Otolaryngology-Head & Neck Surgery*, 117(3), 321-326 (1991).

Samuels et al., *Molecular and Cellular Biology*, 13(10), 6241-6252 (1993).

Samulski et al., *Journal of Virology*, 63(9), 3822-3828 (1989).

Sarubbi et al., *Analytical Biochemistry*, 237(1), 70-75 (1996).

Sata et al., *The Journal of Biological Chemistry*, 273(50), 33103-33106 (1998).

Schaap et al., *The Journal of Biological Chemistry*, 268(27), 20232-20236 (1993).

Schneider et al., *Tetrahedron Letters*, 31(3), 335-338 (1990).

Seth et al., *The Journal of Biological Chemistry*, 266(35), 23521 (1991).

Siebenlist et al., *Cell*, 20(1), 269 (1980).

Siegel et al., *The Journal of Immunology*, 151(8), 4116-4127 (1993).

Smith et al., *Proceedings of the National Academy of Sciences of the United States of America*, 82(24), 8404-8408 (1985).

Smith et al., *Journal of Molecular Biology*, 224(4), 899-904 (1992).

Smith et al., *Advances in Applied Mathematics*, 2(4), 482-489 (1981).

Sozeri et al., *Oncogene*, 7(11), 2259 (1992).

Srinivasula et al., *The Journal of Biological Chemistry*, 272(30), 18542-18545 (1997).

Stein, *Biochimica et Biophysica Acta*, 1489(1), 45-52 (1999).

Stokoe et al., *The Embo Journal*, 11(11), 3985-3994 (1992).

Sturgill et al., *Nature*, 334(6184), 715-718 (1988).

Takamiya et al., *Journal of Neuroscience Research*, 33(3), 493-503 (1992).

Tewari et al., *The Journal of Biological Chemistry* 270(39), 22705-22708 (1995).

Thome et al., *Nature*, 386(6624), 517-521 (1997).

Tilburn et al., *Gene*, 26(2&3), 205-221 (1983).

Traverse et al., *Oncogene*, 8(11), 3175-3181 (1993).

Turner et al., *Proceedings of the National Academy of Sciences of the United States of America*, 90(12), 5544-5548 (1993).

Uhlmann et al., *Chemical Reviews*, 90(4), 543-584 (1990).

Van Den Berg et al., *Bio/Technology*, 8(2), 135139 (1990).

Verhoeyer et al., *Science*, 239(4847), 1534-1536 (1988).

Vile et al., *Cancer Research.*, 53(5), 962-967 (1993).

Vile et al., *Cancer Research*, 53(17), 3860-3864 (1993).
Vincent et al., *Nature Genetics*, 5, 130-134 (1993).
Vlak et al., *The Journal of General Virology*, 69(4) 765-776 (1988).
Warne et al., *Nature*, 364(6435), 352-355 (1993).
Weiss et al., *Journal of the National Cancer Institute*, 23, 51-54 (1998).
Welling et al., *FEBS Letters*, 188(2), 215-218 (1985).
Winitz et al., *The Journal of Biological Chemistry*, 268(26), 19196-19199 (1993).
Woffendin, *Proceedings of the National Academy of Sciences of the United States of America*, 91(24), 11581-11585 (1994).
Wotten et al., *The Journal of Biological Chemistry*, 268(24), 17975-17982 (1993).
Wu, *The Journal of Biological Chemistry*, 264(29), 16985-16987 (1989).
Yeh et al., *The Journal of Experimental Medicine*, 188(10), 1795-1802 (1998).
Yelton et al., *Proceedings of the National Academy of Sciences of the United States of America*, 81(5), 1470-1474 (1984).
Zabner et al., *Cell*, 75(2), 207-216 (1993).
Zhang et al., *Nature*, 364(6435), 308-313 (1993).
Buruham et al., *American Journal of Hospital Pharmacy* 51(2), 210-218 (1994).
Caillaud et al., *European Journal of Neuroscience*, 5(10), 1287-1291 (1993).
Caplen et al., *Proceedings of the National Academy of Sciences of the United States of America*, 98(17) 9742-47 (2001).
Carbonell et al., *Gene*, 73(2), 409-418 (1988).
Carroll et al., *The Journal of Biological Chemistry* 266(23) 14964-14969 (1991).
Carprino et al., *The Journal of Organic Chemistry*, 37, 3404-3409 (1972).
Chang et al., *Nature*, 275(5681), 617-624 (1978).
Chin, "On the preparation and utilization of isolated and purified oligonucleotides", Katherine R. Everett Law Library of the University of North Carolina, Mar. 2002 (on a CD).
Chinnaiyan et al., *The Journal of Biological Chemistry*, 271(9) 4961-4965 (1996).
Chiou et al., *Virology*, 244(1), 108-118 (1998).
Chothia et al., *Journal of Molecular Biology*, 196(4) 901-917 (1987).
Chung et al., *Proceedings of the National Academy of Sciences of the United States of America*, 88(11), 4981- (1991).
Cleland et al., *Critical Reviews in Therapeutic Drug Carrier Systems*, 10(4), 307-377 (1993).
Connelly, *Human Gene Therapy*, 6(2), 185-193 (1995).
Corpet et al., *Nucleic Acids Research.*, 16(22), 10881-10890 (1988).
Cregg et al., *Molecular and Cellular Biology*, 5(12), 3376-3385 (1985).
Crooke, *Biochimica et Biophysica Acta*, 1489(1) 31-44 (1999).
Cunningham et al., *Science*, 244(108), 1081-1085 (1989).
Curiel et al., *Human Gene Therapy*, 3(2), 147-154 (1992).
Darzynkiewicz et al., *Cytometry*, 13(8), 795-808 (1992).
Das et al., *Journal of Bacteriology*, 158(3), 1165-1167 (1984).
Davidow et al., *Current Genetics*, 10(1), 39-48 (1985).
Davis et al., *Enzyme Engineering*, 4, 169-73 (1978).
Dayhoff et al., *Atlas of Protein Sequence and Structure*, 5(Supplement 3), 345-352 (1978).
De Bohr et al., *Proceedings of the National Academy of Sciences of the United States of America*, 80(1), 21-25 (1983).
De Louvencourt et al., *Journal of Bacteriology*, 154(2), 737-742 (1983).
De Vos et al., *Science*, 255(5042), 306-312 (1992).
Dijkema et al., *The EMBO Journal*, 4(3), 761 (1985).
Earl et al., *Proceedings of the National Academy of Sciences of the United States of America*, 83(11), 3659-3663 (1986).
Elbashir et al., *Nature*, 411 (6836), 494-98 (2001).
Fabian et al., *Molecular and Cellular Biology*, 13(11), 7170 (1993).
Federoff et al., *Proceedings of the National Academy of Sciences of the United States of America*, 89(5), 1636-40 (1992).
Felger et al., *Human Gene Therapy*, 7(15), 1791-1793 (1996).
Fink et al., *Annual Review of Neuroscience*, 19, 265-87 (1992).
Flotte et al., *Proceedings of the National Academy of Sciences of the United States of America*, 90(22), 10613-10617 (1993).
Friden et al., *Science*, 259, 373-377 (1993).
Friesen et al., *The Molecular Biology of Baculoviruses*, 31-49 (1986).
Gaillardin et al., *Current Genetics*, 10, 49-58 (1985).
Galfre et al., *Methods in Enzymology; Immunochemical Techniques*, 73, 3-46 (1981).
Gardner et al., *The Journal of Biological Chemistry*, 268(24) 1789617901 (1993).
Gille et al., *Nature*, 358(6385), 414-417 (1992).
Gleeson et al., *The Journal of General Microbiology*, 132(12), 3459-3465 (1986).
Goeddel et al., *Nature*, 281(5732), 544 (1979).
Goeddel et al., *Nucleic Acids Research*, 8(18), 4057-4074 (1980).
Goltsev et al., *The Journal of Biological Chemistry*, 272(32), 19641-19644 (1997).
Gonzalez et al., *Current Opinion in Biotechnology*9(6), 624-631 (1998).
Gorman et al., *Proceedings of the National Academy of Sciences of the United States of America*, 79(22), 6777-6781 (1982).
Griffith et al., *The Journal of Immunology*, 161(6), 2833-2840 (1998).
Guzman et al., *Circulation Research*, 73(6), 1202-1207 (1993).
Guzman et al., *Circulation*, 88(6), 2838-2848 (1993).
Ham et al., *Methods in Enzymology*, 58, 44-93 (1979).
Han et al., *American Journal of Respiratory Cell and Molecular Biology*, 11(3), 270-278 (1994).
Heo et al., *Cancer Research*, 49(18), 5167-5175 (1989).
Higgins et al., *Computer Applications in the Biosciences*, 8(2), 189-191 (1992).
Hinnen et al., *Proceedings of the National Academy of Sciences*, 75(4), 1929-1933 (1978).
Horrevoets et al., *Blood*, 93(10), 3418-3431 (1999).
Hu et al., *Virology*, 227(2), 295-304 (1997).
Hu et al., *The Journal of Biological Chemistry*, 272(15), 9621-9624 (1997).
Hu et al., *The Journal of Biological Chemistry*, 272(28), 17255-17257 (1997).
Inbal et al., *Nature*, 390(6656), 180-184 (1997).
Irmier et al., *Nature*, 388(6638), 190-195 (1997).
Ito, et al., *Journal of Bacteriology*, 153(1), 163-168 (1983).
Jaffe et al., *Nature Genetics*, 1(5), 372-378 (1992).
Jolly, *Cancer Gene Therapy*, 1(1), 51-64 (1994).
Jones et al., *Nature*, 321(6069), 522-525 (1986).
Kaplitt, *Nature Genetics*8(2), 148-154 (1994).
Kasid et al., *Molecular and Cellular Biochemistry*, 173(1&2), 193-197 (1997).
Kasid et al., *Apoptosis Genes*, Kluwer Academic Publishers, MA (eds. Potten, Booth, & Wilson), 85-118 (1998).
Kass-Bisler et al., *Proceedings of the National Academy of Sciences of the United States of America*90(24), 11498-11502 (1993).
Kataoka et al., *The Journal of Immunology*, 161(8), 3936-3942 (1998).
Kelly et al., *The EMBO Journal*, 4(2), 475-479 (1985).
Kettleborough et al., *Protein Engineering.*, 4(7), 773-83 (1991).
Kimura, *Human Gene Therapy*, 5(7), 845-852 (1994).
Kissil et al., *The EMBO Journal*, 18(2), 353-362 (1999).
Kizaka-Kondoh et al., *Molecular and Cellular Biology*, 12(11), 5078-5086 (1992).
Koide et al., *Proceedings of the National Academy of Sciences of the United States of America*, 90(18), 8683 (1993).
Kolls et al., *Proceedings of the National Academy of Sciences of the United States of America*, 91(1), 9215-219 (1994).
Krug et al., *Methods in Enzymology; Guide to Molecular Cloning Techniques*, 152, 316-325 (1987).
Kumar et al., *The Journal of Biological Chemistry*, 275(4) 2973-2978 (2000).
Kunze et al., *Journal of Basic Microbiology*, 25(2), 141-144 (1985).
Kurtz et al., *Molecular and Cellular Biology*, 6(1), 142 (1986).
Lebacq-Verheyden et al., *Molecular and Cellualr Biology*, 8(8), 3129 (1988).

Lee et al., *The Journal of Biological Chemistry*, 266(16), 10351-10357 (1991).
Lennon et al., *Genomics*, 33(1), 151-152 (1996).
Levero et al., *Gene*, 101(2), 195-202 (1991).
Li et al., *Human Gene Therapy*, 4(4), 403-409 (1993).
Li et al., *Proceedings of the National Academy of Sciences*, 90(20), 9247-9251 (1993).
Luckow et al., *Bio/Technology*, 6(1), 47-55 (1988).
MacDonald et al., *Molecular and Cellular Biology*, 13(11), 6615-6620 (1993).
Maeda et al., *Nature*, 315(6020), 592-594 (1985).
Martens et al., *Analytical Biochemistry*, 273(1), 20-31 (1999).
Martin et al., *DNA*, 7(2), 99-106 (1988).
Mendelson et al., *Virology*, 166, 154-165 (1988).
Merrifield et al., *Journal of the American Chemical Society*, 85, 2149-2154 (1963).
Miller et al., *Genetic Engineering*, 8, 277-279 (1986) (Setlow et al. ed.).
Miller, *Annual Review of Microbiology*, 42, 177-199 (1988).
Milner et al., *Nature Biotechnology*, 15, 537-541 (1997).
Milstein et al., *Nature*, 256(5517), 495-497 (1975).
Miyajima et al., *Gene*, 58(2&3), 273-281 (1987).
Morimoto et al., *The Journal of Immunology*, 147(8), 2609-2616 (1991).
Morrison et al., *The Journal of Biological Chemistry*, 268(23), 17309-17316 (1993).
Morrison et al., *Proceedings of the National Academy of Sciences of the United States of America*, 81(21), 6851-6855 (1984).
Morrison et al., *Advances in Immunology*, 44, 65-92 (1988).
U.S. Appl. No. 60/264,062, filed Jan. 26, 2001, Kumar et al.
U.S. Appl. No. 60/281,780, filed Apr. 6, 2001, Kasid et al.
U.S. Appl. No. 60/382,031, filed May 22, 2002, Gokhale et al.
U.S. Appl. No. 60/371,126, filed Apr. 10, 2002, Kasid et al.
U.S. Appl. No. 60/281,779, filed Apr. 6, 2001, Kasid et al.
U.S. Appl. No. 60/281,785, filed Apr. 6, 2001, Kasid et al.
U.S. Appl. No. 60/371,116, filed Apr. 10, 2002, Kasid et al.
U.S. Appl. No. 60/281,796, filed Apr. 6, 2001, Kasid et al.
U.S. Appl. No. 10/056,210, filed Jan. 28, 2002, Kasid et al.
U.S. Appl. No. 10/411,931, filed Apr. 10, 2003, Kasid et al.
U.S. Appl. No. 10/411,930, filed Apr. 10, 2003, Kasid et al.
U.S. Appl. No. 10/443,273, filed May 22, 2003, Gokhale et al.
U.S. Appl. No. 10/627,571, filed Jan. 28, 2002, Kasid et al.
U.S. Appl. No. 10/679,561, filed Oct. 6, 2003, Kasid et al.
U.S. Appl. No. 10/679,865, filed Oct. 6, 2003, Kasid et al.
U.S. Appl. No. 10/680,313, filed Oct. 6, 2003, Kasid et al.
U.S. Appl. No. 10/679,580, filed Oct. 6, 2003, Kasid et al.
Agrawal, *Biochimica et Biophysica Acta*, 1489(1), 53-68 (1999).
Altschul et al., *Nucleic Acids Research*, 25(17), 3389-3402 (1997).
Alvarez et al., *The Journal of Biological Chemistry*, 266(23), 15277-15285 (1991).
Ashkenazi et al., *Science*, 281(5381), 1305-1308 (1998).
Barba et al., *Journal of Neurosurgery*, 79(5), 729-735 (1993).
Baccarini et al., *The Journal of Biological Chemistry*, 266(17), 10941-10945 (1991).
Bain et al., *Gene Therapy*, 1(S68), (1994).
Ballance et al., *Biochemical and Biophysical Research Communications*, 112(1), 284-289 (1983).
Barnes et al., *Analytical Biochemistry*, 102(2), 255 (1980).
*Basic and Clinical Immunology*, 217-262 (Sites and Terr eds., Appleton & Lange, Norwalk, CT 1991).
Beach et al., *Nature*, 300(5894), 706-709 (1981).
Belyavsky et al., *Nucleic Acids Research* 17(8), 2919-2932 (1989).
Berkner, *BioTechniques*, 6(7), 616-629 (1988).
Berns et al., *Annals of The New York Academy of Sciences*, 772, 95-104 (1995).
Bertin et al., *Proceedings of the National Academy of Sciences of the United States of America*, 94(4), 1172-1176 (1997).
Blundell et al., *Nature*, 326(6111), 347-352 (1987).
Boldin et al., *Cell*; 85(6), 803-815 (1996).
Boshart et al., *Cell*, 41(2), 521 (1985).
Bowie et al., *Science*, 247(4948), 1306-1310 (1990).
Branch et al., *Trends in Biochemical Sciences*, 23(266), 45-50 (1998).

\* cited by examiner

SHINC-3

```
  1  catagataaa tttaggggga ttggatgtat tattcaactt tgatttgggt
 51  tgtaaaatgt gttaaatcct gttcattgaa ctcccatcaa ctcttataaa
101  attcatgctg atcttcatta ccgttgcatg attggaaatg tttaaaacat
151  tgtacagttt tagtatagag aaatgtaatg gtttttgtga c (SEQ ID NO:1)
```

Figure 4.

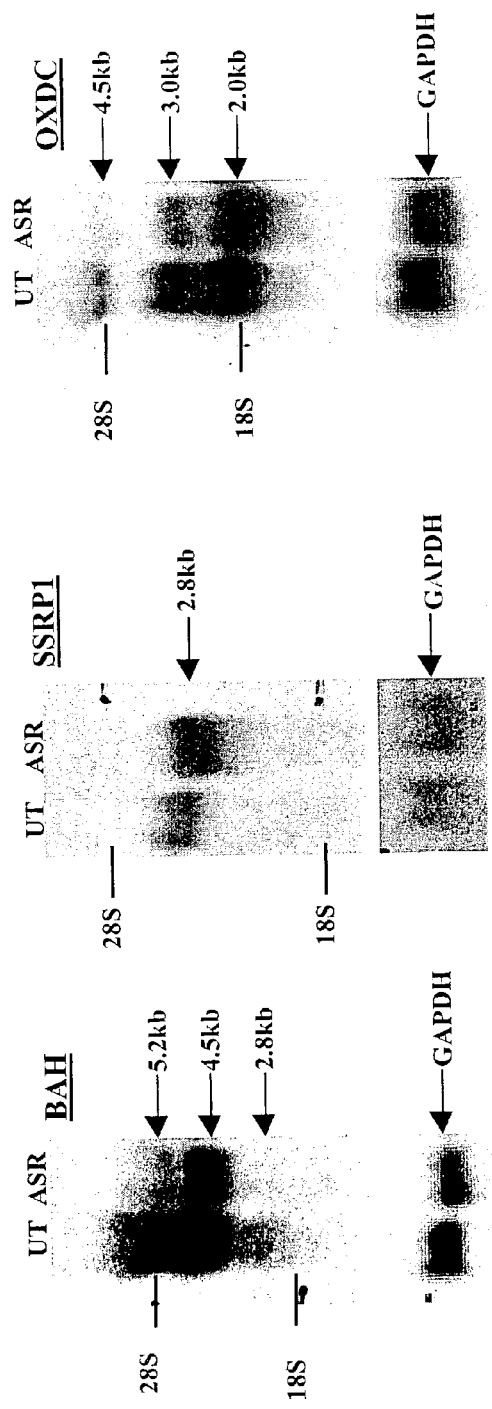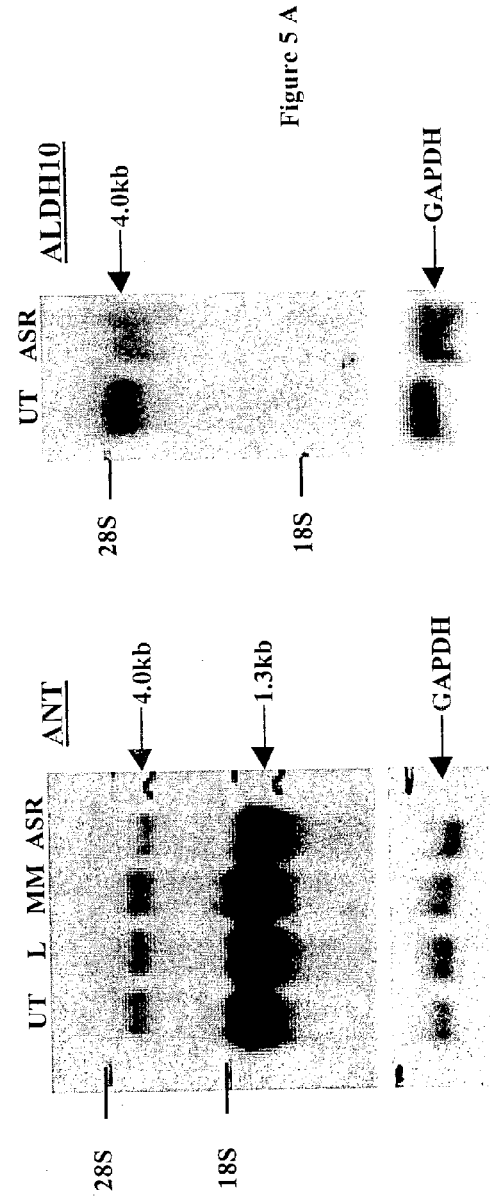
Figure 5 A

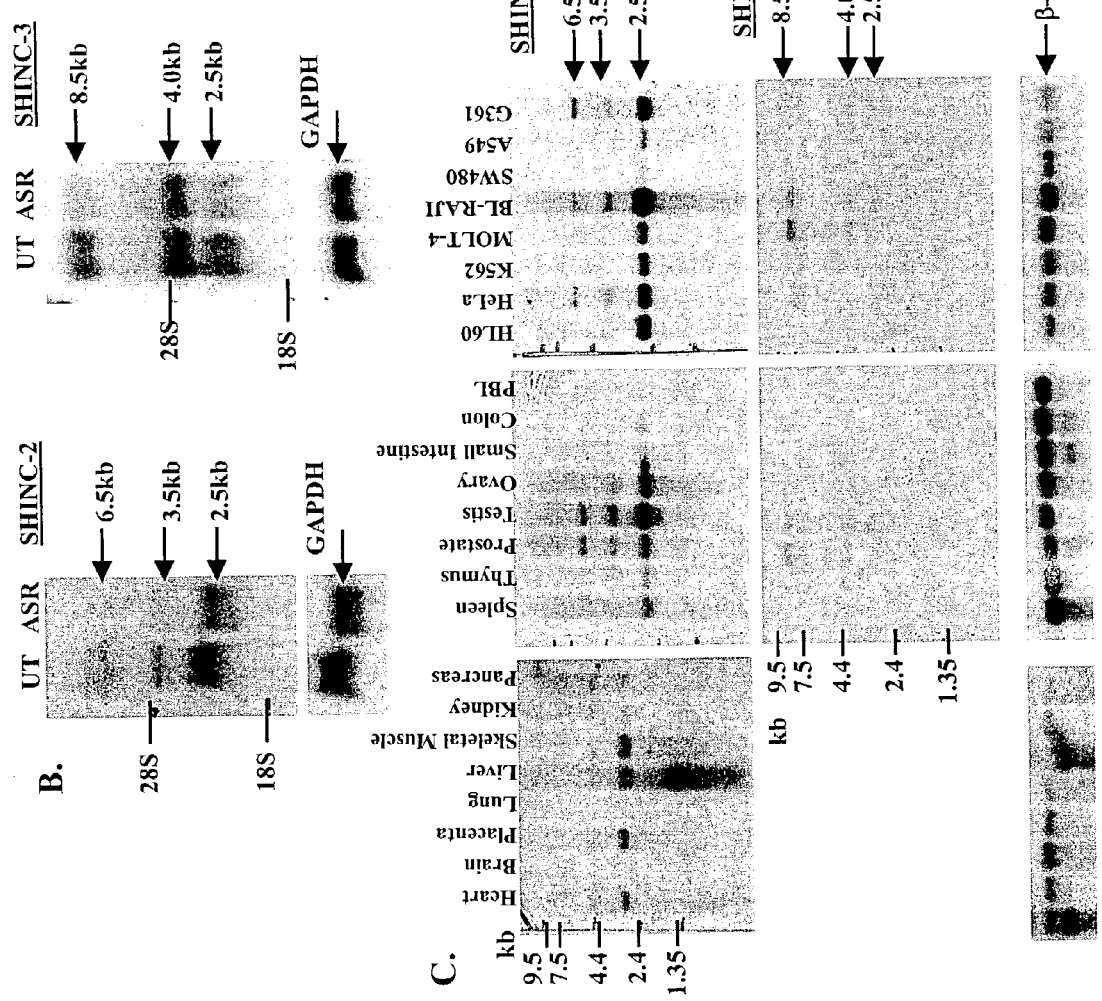
Figures 5 B and 5C

```
                aataacctgg agccggcggc gtaggtggc tctttagggc ttcaccccga agctccacct    60
                tcgctcccgt ctttctgaa acacccgttt gacctcggcg gtcgggaca ggtacctccc   120
                ggctgctgcg ggtgcccgg atccagtcgg ctgcaccagg cgacgagac ccttcccgg    180
                tggaggctca gagttccgc agggtgcatc cggcctgtgt gtgcgcgag gcaggaagc    240
                cggtacccgg gtcctgcc cagcgctgac gtttctctc ccctttcttc tctctcgcg    300
                gttgggcgt cgcagacgct agtgtgagcc ccc                               333

1   M   A   D   T   T   P   N   G   P   Q   G   A   G   A   V   Q   F   M   M   T
      atg gca gat acg acc ccg aac ggc ccc caa ggg gcg ggc gct gtg caa ttc atg atg acc   393
 21   N   K   L   D   T   A   M   W   L   S   R   L   F   T   V   C   S   A   L
      aat aaa ctg gac acg gca atg tgg ctt tct cgc ttg ttc aca gtt tac tgc tct gct ctg   453
 41   F   V   L   P   L   L   G   L   H   E   A   A   S   F   Y   Q   R   A   L   L
      ttt gtt ctg cct ctt ctt ggg ttg cat gaa gca gca agc ttt tac caa cgt gct ttg ctg   513
 61   A   N   A   L   T   S   A   L   R   L   H   Q   R   L   P   H   F   Q   L   S
      gca aat gct ctt acc agt gct ctg agg ctg cat caa aga tta cca cac ttc cag tta agc   573
 81   R   A   F   L   A   Q   A   L   L   E   D   S   C   H   Y   L   L   Y   S   L
      aga gca ttc ctg gcc cag gct ttg tta gag gac agc tgc cac tac ctg ttg tat tca ctc   633
101   I   F   V   N   S   Y   P   V   T   M   S   I   F   P   V   L   L   F   S   L
      atc ttt gta aat tcc tat cca gtt aca atg agt atc ttc cca gtc ttg tta ttc tct ttg   693
121   L   H   A   A   T   Y   A   T   A   V   L   D   K   V   L   S   A   N   L   P
      ctt cat gct gcc aca tat gct gtc ttg gac aaa tta agt gct gac gca agg ggc tca aat   753
141   L   R   S   V   L   D   K   L   S   A   N   Q   N   L   K   F   I
      ctg cga aga tct gtc ttg gac aaa tta agt gct aat caa caa aat ctg aaa ttc att       813
161   A   C   N   E   I   F   L   M   P   A   T   V   F   M   L   F   S   G   Q   G
      gct tgc aat gaa ata ttc ctg atg cct gcg aca gtt atg ctt ttt agt ggt caa gga       873
181   S   L   L   Q   P   F   I   Y   Y   R   F   L   T   L   R   Y   S   S   R   R
      agt ttg ctc caa cct ttt ata tac tat aga ttt ctt acc ctt cga tat tcg tct cga aga   933
201   N   P   Y   C   R   T   L   F   N   E   L   R   I   V   E   H   I   I   M
      aac cca tat tgt cgg acc tta ttt aat gaa ctg agg att gtt gaa cac ata ata atg       993
221   K   P   A   C   P   L   F   V   R   R   L   C   L   Q   S   I   A   F   I   S
      aaa cct gct tgc cca ctg ttt gtg aga aga ctt tgt ctc cag agc att gcc ttt ata agc  1053
241   R   L   A   P   T   V   P   *   (SEQ ID NO:3)
      aga ttg gca cca aca gtt cca tag                                                  1113
```

Figure 7

```
ttaacatcta gttaagctac aaatatagta taagcattat tagcagctgg tacttctgct  1138
aggggttgta aattccaggt gttacactga cctcaatcca attacataa tttacataaa   1198
tgcatctcgg tggaaaaata atcattttct tggcatgtta aatcaagctt aaaaagtttt  1258
gagaaaattt tactgtgctg tgttgctaat ggttaaagaa gtctgtatct agtgataaat  1318
ataccagttt ttttaaaaag atgctgttgt gcctatatca tgaagtacat taatttctca  1378
tgtaaaaaaa atagctctaa aatttgtttc aacctaattg gtaacctgag tttatatctg  1438
gcatgaattc attatggtga tacacatatg tgaattcagt acatttgag acagtattct   1498
accattcagt aattttggtt aatgatttta acacttctca gtgtatttaa tttcaaattg  1558
ttttttttaat tggttttatg ctgcttgtt aggacagatg tgtttgaat gtaccattat   1618
aagaagaatt ctatgtatct taaactatga tctctaaaa tttatttcc gtaagtactt    1678
ctgtggcctt gagtatttt taaaaggctc aactgtaagc ctcctagcca gttggataaa   1738
tatttgggt cacctagcca ttgaaagcag aagcagtag tgacacagct ttcccttcaa    1798
agagccattg agaaacattt ctcaaacagg aaatcctct tttactaatg tggacatata   1858
gattattcgt attatagttt gtagaactac ctagttcaga atcttgactg ccagttttct  1918
tggttcctta ggcttgaatt ttcatagaca atgcaacag tttagatgcc tttgaaagg    1978
aatgtaatga agattcagca tctgactata tgtgtgtcta tcctgaaata ataatggaga  2038
gtatactgta gattacatgt ttaccatca aatctgactt aaaagttaa atggaagtt     2098
ttatagtaa ggtaattgat tgggaatggg gtaggggag gagtgtggg ggaataatgt     2158
gcattcagt ctcaacgcat agataaattt aggggaattg gatgcattat tcaacttga    2218
tttgggttgt aaaatgtgtt aaatcctgtt cattgaacto ccatcaacto ttatgaaatt  2278
catgctgatc ttcattaccg ttgcatgatt ggaaatgttt aaaacattgt acagtttag   2338
tatagagaaa tgtaatggtt tttgtgacca gtttctgtct gcatgtaatt tggattcctc  2398
aaatacattc attagtaatt tatcagtaac attagttta tttttgttca tctccctatc   2458
tataaaaagg ggatattctt aggataaata catgaaaaat tatacttgat agcttaacta  2518
taatcagcta ttttgtatt tttgtaatat ttgtccacta agctgagaa gcagcctcat    2578
acagttgatt ttgctatgt ggctagtctt attgtcacta tgtaagtaat ccaatgtttt   2638
tagaaactaa actttctaga gcaataaaat gactataatg ttaagt (SEQ ID NO:2)   2684
```

Figure 7 (continued)

SEQUENCE LISTING

<160> NUMBER OF SEQ ID NOS: 3

<210> SEQ ID NO 1
<211> LENGTH: 191
<212> TYPE: DNA

```
<213> ORGANISM: Homo sapiens

<400> SEQUENCE: 1
catagataaa tttaggggaa ttggatgtat tattcaactt tgatttgggt tgtaaaatgt      60
gttaaatcct gttcattgaa ctcccatcaa ctcttataaa attcatgctg atcttcatta     120
ccgttgcatg attggaaatg tttaaaacat tgtacagttt tagtatagag aaatgtaatg     180
gtttttgtga c                                                         191

<210> SEQ ID NO 2
<211> LENGTH: 2683
<212> TYPE: DNA
<213> ORGANISM: Homo sapiens

<400> SEQUENCE: 2
aataacctgg agccggcggc gtaggttggc tctttagggc ttcaccccga agctccacct      60
tcgctcccgt ctttctggaa acaccgcttt gatctcggcg gtgcgggaca ggtacctccc     120
ggctgctgcg ggtgccctgg atccagtcgg ctgcaccagg cgagcgagac ccttccctgg     180
tggaggctca gagttccggc agggtgcatc cggcctgtgt gtggcgcgag cagggaagc      240
cggtacccgg gtcctggccc cagcgctgac gttttctctc ccctttcttc tctcttcgcg     300
gttgcggcgt cgcagacgct agtgtgagcc cccatggcag atacgacccc gaacggcccc     360
caaggggcgg gcgctgtgca attcatgatg accaataaac tggacacggc aatgtggctt     420
tctcgcttgt tcacagttta ctgctctgct ctgtttgttc tgcctcttct tgggttgcat     480
gaagcagcaa gcttttacca acgtgctttg ctggcaaatg ctcttaccag tgctctgagg     540
ctgcatcaaa gattaccaca cttccagtta agcagagcat tcctggccca ggctttgtta     600
gaggacagct gccactacct gttgtattca ctcatctttg taaattccta tccagttaca     660
atgagtatct tcccagtctt gttattctct ttgcttcatg ctgccacata tacgaaaaag     720
gtccttgacg caagggctc aaatagttta cctctgctga tctgtcttt ggacaaatta      780
agtgctaatc aacaaaatat tctgaaattc attgcttgca atgaaatatt cctgatgcct     840
gcgacagttt ttatgctttt tagtggtcaa ggaagtttgc tccaaccttt tatatactat     900
agatttctta cccttcgata ttcgtctcga agaaacccat attgtcggac cttatttaat     960
gaactgagga ttgttgttga acacataata atgaaacctg cttgcccact gtttgtgaga    1020
agactttgtc tccagagcat tgcctttata agcagattgg caccaacagt tccatagtta    1080
acatctagtt aagctacaaa tatagtataa gcattattag cagctggtac ttctgctagg    1140
ggttgtaaat tccaggtgtt acactgacct caatccaatt tacataattt acataaatgc    1200
atctcggtgg aaaaataatc attttcttgg catgttaaat caagcttaaa aagttttgag    1260
aaaatttttac tgtgctgtgt tgctaatggt taagaagtc tgtatctagt gataaatata    1320
ccagtttttt taaaaagatg ctgttgtgcc tatatcatga agtacattaa tttctcatgt    1380
aaaaaaaata gctctaaaat ttgtttcaac ctaattggta acctgagttt atatctggca    1440
tgaattcatt atggtgatac acatatgtga attcagtaca ttttgagaca gtattctacc    1500
attcagtaat tttggttaat gattttaaca cttctcagtg tatttaattt caaattgttt    1560
ttttaattgg ttttatgctg ctttgttagg acagatgtgt tttgaatgta ccattataag    1620
aagaattcta tgtatcttaa actatgatct tctaaaattt tatttccgta agtacttctg    1680
tggccttgag tattttttaa aaggctcaac tgtaagcctc ttagccagtt ggataaatat    1740
ttgggtcac ctagccattg aaagcagaaa gcagtagtga cacagctttc ccttcaaaga     1800
```

```
gccattgaga acatttctc aaacaggaaa tccttctttt actaatgtgg acatatagat    1860
tattcgtatt atagtttgta gaactaccta gttcagaatc ttgactgcca gttttcttgg    1920
tttcttaggc ttgaattttc atagacaatt gcaacagttt agatgccttt tgaaaggaat    1980
gtaatgaaga ttcagcatct gactatatgt gtgtctatcc tgaataata atggagagta    2040 tactgtagat tacatgttta cccatcaaat ctgacttaaa aggttaaatg gaaggtttta    2100
taggtaaggt aattgattgg gaatggggta gggggaggag ttgtggggga ataatgtgca    2160
tttcagtctc aacgcataga taaatttagg ggaattggat gcattattca actttgattt    2220
gggttgtaaa atgtgttaaa tcctgttcat tgaactccca tcaactctta tgaaattcat    2280
gctgatcttc attccgttg catgattgga aatgtttaaa acattgtaca gttttagtat    2340
agagaaatgt aatggttttt gtgaccagtt tctgtctgca tgtaatttgg atttctcaaa    2400
tacattcatt agtaatttat cagtaacatt agttttatt ttgttcatct ccttatctat    2460
aaaaagggga tattcttagg ataaatacat gaaaaattat acttgatagc ttaactataa    2520
tcagctattt ttgtattttt gtaatatttt tccactaagc tggagaagca gcctcataca    2580
gttgattttg tgtatgtggc tagtcttatt gtcactatgt aagtaatcca atggttttag    2640
aaactaaact ttctagagca ataaaatgac tataatgtta agt                      2683

<210> SEQ ID NO 3
<211> LENGTH: 247
<212> TYPE: PRT
<213> ORGANISM: Homo sapiens

<400> SEQUENCE: 3

Met Ala Asp Thr Thr Pro Asn Gly Pro Gln Gly Ala Gly Ala Val Gln
1               5                   10                  15

Phe Met Met Thr Asn Lys Leu Asp Thr Ala Met Trp Leu Ser Arg Leu
            20                  25                  30

Phe Thr Val Tyr Cys Ser Ala Leu Phe Val Leu Pro Leu Leu Gly Leu
        35                  40                  45

His Glu Ala Ala Ser Phe Tyr Gln Arg Ala Leu Leu Ala Asn Ala Leu
    50                  55                  60

Thr Ser Ala Leu Arg Leu His Gln Arg Leu Pro His Phe Gln Leu Ser
65                  70                  75                  80

Arg Ala Phe Leu Ala Gln Ala Leu Leu Glu Asp Ser Cys His Tyr Leu
                85                  90                  95

Leu Tyr Ser Leu Ile Phe Val Asn Ser Tyr Pro Val Thr Met Ser Ile
            100                 105                 110

Phe Pro Val Leu Leu Phe Ser Leu Leu His Ala Ala Thr Tyr Thr Lys
        115                 120                 125

Lys Val Leu Asp Ala Arg Gly Ser Asn Ser Leu Pro Leu Leu Arg Ser
    130                 135                 140

Val Leu Asp Lys Leu Ser Ala Asn Gln Gln Asn Ile Leu Lys Phe Ile
145                 150                 155                 160

Ala Cys Asn Glu Ile Phe Leu Met Pro Ala Thr Val Phe Met Leu Phe
                165                 170                 175

Ser Gly Gln Gly Ser Leu Leu Gln Pro Phe Ile Tyr Tyr Arg Phe Leu
            180                 185                 190

Thr Leu Arg Tyr Ser Ser Arg Arg Asn Pro Tyr Cys Arg Thr Leu Phe
        195                 200                 205

Asn Glu Leu Arg Ile Val Val Glu His Ile Ile Met Lys Pro Ala Cys
```

-continued

```
            210                 215                 220
Pro Leu Phe Val Arg Arg Leu Cys Leu Gln Ser Ile Ala Phe Ile Ser
225                 230                 235                 240

Arg Leu Ala Pro Thr Val Pro
                245
```

GENE SHINC-3 AND DIAGNOSTIC AND THERAPEUTIC USES THEREOF

CROSS-REFERENCE TO RELATED APPLICATIONS

This application claims priority to U.S. Provisional Patent Application No. 60/371,116, filed on Apr. 10, 2002.

STATEMENT REGARDING FEDERALLY SPONSORED RESEARCH AND DEVELOPMENT

This invention was made in part with Government support under Grant Numbers CA68322 and CA74175 awarded by the National Institutes of Health. The Government has certain fights in this invention.

FIELD OF THE INVENTION

The present invention relates to a gene that encodes a polypeptide involved in apoptosis. This polypeptide is a useful target for identifying compounds that modulate cancer progression by modulating apoptosis. Also, this polypeptide is useful as a diagnostic target for detecting cancers wherein the expression of this polypeptide varies from its expression levels in non-cancerous cells. In addition, the gene of the invention may play a role in cell proliferation and growth.

BACKGROUND OF THE INVENTION

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

Oligonucleotides have been employed as therapeutic moieties in the treatment of disease states in animals and man. For example, workers in the field have now identified antisense, triplex and other oligonucleotide compositions that are capable of modulating expression of genes implicated in viral, fungal and metabolic diseases. Tisense oligonucleotide inhibition of gene expression has proven to be a useful tool in understanding the roles of raf genes. An antisense oligonucleotide complementary to the first six codons of human c-raf has been used to demonstrate that the mitogenic response of T cells to interleukin-2 (IL-2) requires c-raf. Cells treated with the oligonucleotide showed a near-total loss of c-raf protein and a substantial reduction in proliferative response to IL-2. Riedel et al., Eur. J. Immunol. 1993, 23, 3146-3150. Rapp et al. have disclosed expression vectors containing a raf gene in an antisense orientation downstream of a promoter, and methods of inhibiting raf expression by expressing an antisense Raf gene or a mutated Raf gene in a cell. WO application 93/04170. An antisense oligodeoxyribonucleotide complementary to codons 1-6 of murine c-Raf has been used to abolish insulin stimulation of DNA synthesis in the rat hepatoma cell line H4IIE. Tornkvist et al., J. Biol. Chem. 1994, 269, 13919-13921. WO Application 93/06248 discloses methods for identifying an individual at increased risk of developing cancer and for determining a prognosis and proper treatment of patients afflicted with cancer comprising amplifying a region of the c-raf gene and analyzing it for evidence of mutation. Denner et al. discloses antisense polynucleotides hybridizing to the gene for raf, and processes using them. WO 94/15645. Oligonucleotides hybridizing to human and rat raf sequences are disclosed. Iversen et al. discloses heterotypic antisense oligonucleotides complementary to raf which are able to kill ras-activated cancer cells, and methods of killing raf-activated cancer cells. Numerous oligonucleotide sequences are disclosed, none of which are actually antisense oligonucleotide sequences.

Other approaches to the therapeutic control of the proliferation and death of cancerous cells involve small molecular weight chemical agents that play a role in modulating apoptosis. One such molecule is Tempo. The present inventors have recently shown that tempo, a low molecular weight antioxidant, is a novel inducer of apoptosis (Suy et al, JBC, 273:17871, 1998, and International Application No. PCT/US99/14173; the contents of which are hereby incorporated by reference in their entirety). Tempo-treatment of tumor-bearing athymic mice causes tumor growth arrest or tumor regression. It is therefore desirable to identify genes the expression of which may be modulated by exposition to Tempo. The identification of such genes is highly beneficial in designing novel gene-based cancer therapeutic and diagnostic protocols.

SUMMARY OF THE INVENTION

The invention provides a SHINC-3 polynucleotide, which can be a nucleic acid encoding all or a portion of a SHINC-3 protein, or a complementary polynucleotide or antisense polynucleotide. In another aspect, the invention provides a SHINC-3 polypeptide, which can be a full-length SHINC-3 protein or a fragment thereof or an analog or homolog thereof Desirably, the SHINC-3 polypeptide modulates apoptosis. In another aspect, the invention provides an antibody that specifically binds a SHINC-3 polypeptide.

In another aspect, the invention provides diagnostic methods. For example, the method affords a method for identifying compounds that modulate apoptosis.

In another aspect, the invention provides a method for detecting or evaluating the prognosis of a cancer. In another aspect, the invention provides diagnostic compositions for detection of cancer.

In another aspect, the invention provides a method of modulating apoptosis or invention or preventing a cancer, tumor growth and/or metastasis by administration of an agent that modulates the expression and/or activity of SHINC-3.

In another aspect, the invention provides formulations of SHINC-3 polynucleotides or proteins. Preferably, such compositions will comprise liposomal formulations.

These aspects of the present invention, as well as additional advantages and inventive features, will be apparent from the accompanying figures and the following detailed description.

DU-145 cells were grown to 80% confluence in improved minimum essential medium (Cellgro) containing 10% fetal bovine serum, followed by treatment with lipofectin, mismatch As-raf oligo or As-raf oligo. After removal of contaminated DNA, the RNA was reverse-transcribed to cDNA with oligo-dT primer, followed by PCR reactions using different combinations of an anchor primer and arbitrary primer. The PCR-amplified oc-[33P]dATP-labeled products were electrophoresed using 6% poly-acrylamide gels, followed by autoradiography. The differentially expressed fragments are indicated by arrows. L, lipofectin; MM, mismatch As-raf ODN; AR, As-raf-ODN; T, 7.5 mM tempo; MMT, mismatch As-raf ODN plus 7.5 mM tempo, ART; As-raf ODN plus 7.5 mM tempo.

FIG. 4. Partial cDNA sequence of SHINC-3 (ASR-25) (SEQ ID NO:1).

FIG. 5. Northern blot hybridization analysis of known and unknown genes expressed in DU-145 cells treated with ASR.

A. Northern blots were sequentially hybridized first with a radiolabeled human partial cDNA probe (ASR-12a, BAH; ASR, 12b, SSRP-1; ASR-13, OXDC; ASR-23, ALDH10), followed by the radiolabeled GAPDH cDNA probe. Various transcript sizes are indicated by arrows.

B. SHINC-2 and SHINC-3 expression in untreated DU-145 cells (UT) and As-raf ODN treated DU-145 cells (ASR). Blots were sequentially probed with SHINC-2 or SHINC-3 cDNA probe, followed by the GAPDH cDNA probe.

C. Comparison of the expression of SHINC-2 (top panels) and SHINC-3 (middle panels) in human normal tissues (Clontech MTN blots 1 and 2) and human cancer cell lines (Clontech). Blots were sequentially probed with radiolabeled SHINC-2, SHINC-3, and p-actin (bottom panels) cDNA probes. HL-60, promyelogenous leukemia; K-562, chronic myelogenous leukemia; MOLT-4, lymphoblastic leukemia; BL-Raji, Burkitt's lymphoma; SW480, colorectal adenocarcinoma; A549, lung carcinoma; G361, melanoma.

Figure 6:
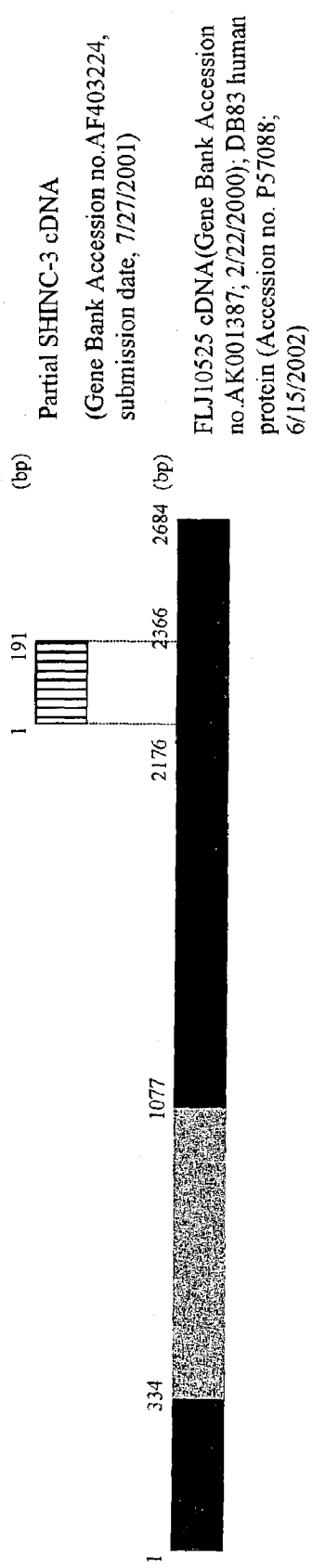

FIG. 6. Schematic map of SHINC-3 cDNA. A 191 bp cDNA fragment, partial SHINC-3 cDNA (hatched box) was isolated by the differential display of mRNA approach from human prostate cancer cell (Du-145) treated with antisense raf oligonucleotide, followed by sequencing (FIG. 4). A homology search of this sequence was used performed and a full length cDNA was identified. The full length cDNA codes for DB83 protein; the ORF is comprised of 247 amino acids. The gray box represents the coding region, 334 bp-1077 bp. The black boxes represent the 5'- and 3'-untranslated regions of cDNA.

FIG. 7. cDNA and predicted amino acid sequences of SHINC-3. A 2684 bp cDNA sequence of SHINC-3 is shown. Nucleotide positions are indicated by numbers on the right. ORF (247 aa) is shown in single letter code. Amino acid positions are numbered on the left. The poly(A)+ signal sequence is underlined (2661-2666 bp). Differential display fragment is shown in bold (2176-2366 bp). The proposed main structure features of the SHINC-3 protein are: transmembrane regions (31-53, 99-121, 158-180 aa); PKC phosphorylation sites (20-22, 127-129, 193-195, 197-199, 198-200 aa); CK2 phosphorylation sites (144-147 aa); and N-myristoylation sites (47-52 aa).

Figure 8:
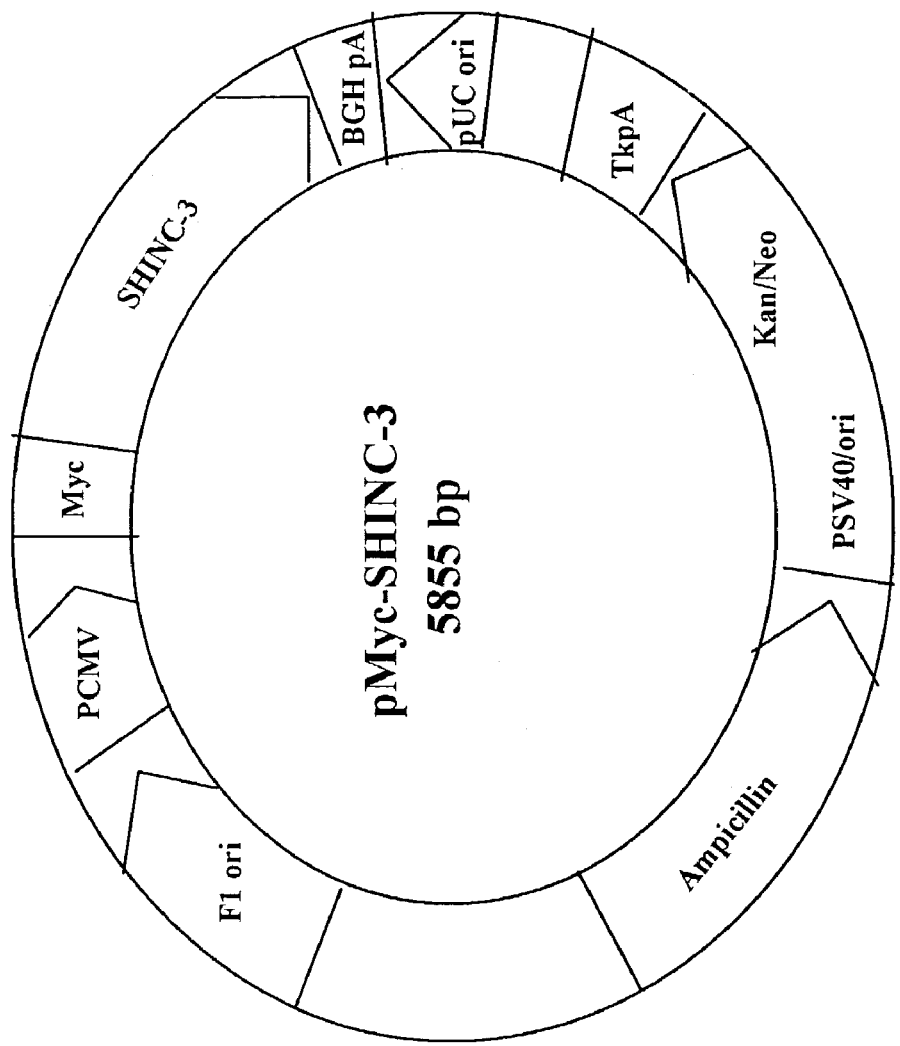

FIG. 8. Schematic map of Myc epitope-tagged SHINC-3 cDNA expression vector (pMYC-SHINC-3). The human testis cDNA was used as a template and SHINC-3 cDNA (ORF) was amplified by RT-PCR and cloned into a pcR3.1 expression vector (Invitrogen). The 5'-primer included the myc tag sequence. PCMV: CMV promoter (1-596 bp), MYC: myc tag sequence (748-781 bp), SHINC-3: SHINC-3 ORF (782-1535 bp); BGH pA: BGH polyadenylation site (1608-1626 bp), pUC ori: pUC origin (1911-2584 bp), TK pA: Thymidine kinase polyadenylation site (2721-2991 bp), Kan/Neo: neomycin/kanamycin resistance gene (ORF) (3166-3957 bp), PSV40/ori: SV40 promoter and origin (3989-4327 bp): Ampicillin: ampicillin resistance gene (ORF) (4406-5266 bp), f1 ori: f1 origin (5397-5853 bp).

Figure 9:
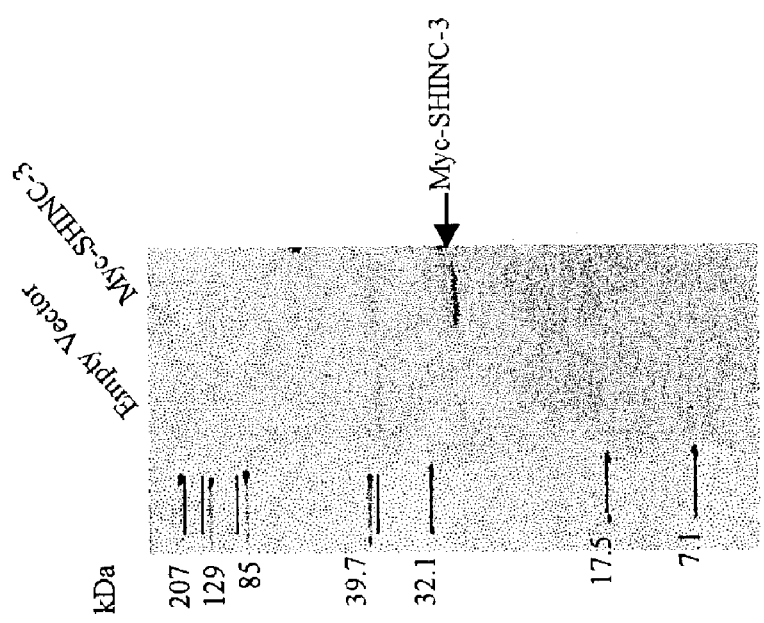

FIG. 9. Expression of myc epitope-tagged SHINC-3 protein (approx 28 kDa) in Cos-1 monkey kidney cells. pMyc-SHINC-3 cDNA was transfected to Cos-1 cells using lipofectamine 2000 (invitrogen). After 48 hr incubation at 37° C., cells were lysed, and the lysate was subjected to 12.5% SDS-polyaclyamide gel electrophoresis, followed by transfer of proteins to PVDF membrane (Millipore). The myc-tagged SHINC-3 protein band was detected by western blotting with mouse monoclonal anti-myc antibody (Santa Cruz), followed by horseradish peroxidase conjugated anti-mouse IgG antibody (Amersham). Arrow indicates myc-tagged SHINC-3 (approx. 28 kDa).

Figure 10:
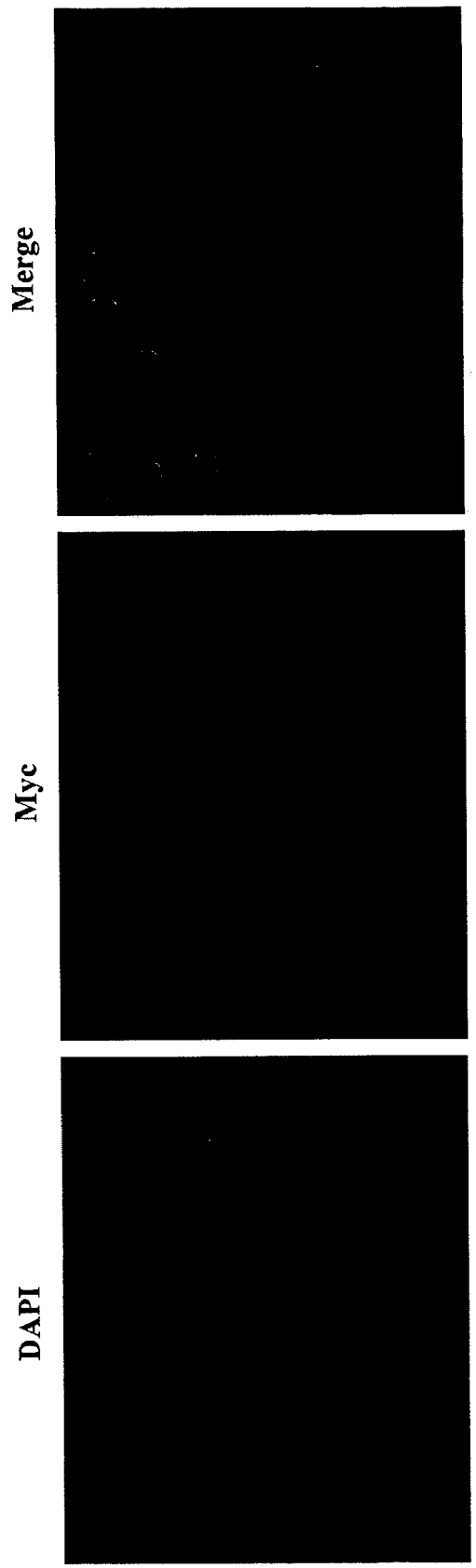

FIG. 10. SHINC-3 protein is located in the cytosol. pMyc-SHINC-3 was transfected to Cos-1 cells with lipofectamine 2000 (invitrogen). After 48 hr incubation at 37° C., the cells were stained with mouse monoclonal anti-myc antibody (Santa Cruz) and Alexa 488 linked anti-mouse IgG antibody (Molecular Probes). Stained cells were observed under immunofluoresent microscope (Nikon).

Figure 11:
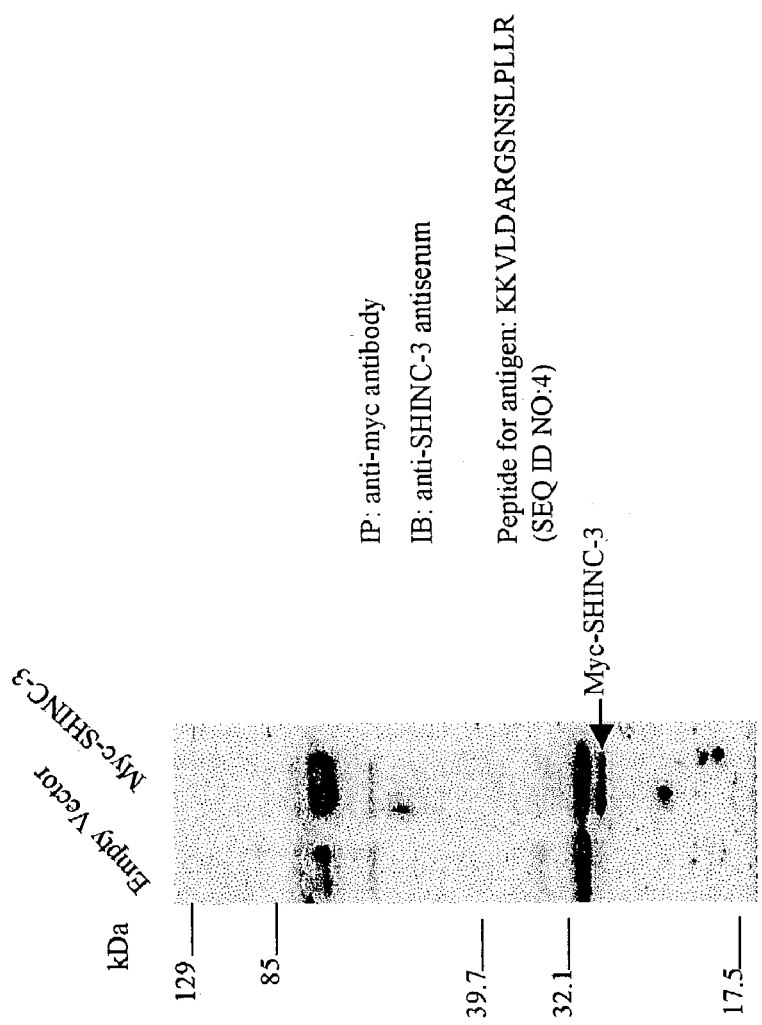

FIG. 11. Development of anti-SHINC-3 antibody. Rabbit SHINC-3 antisera were developed against a SHINC-3-specific peptide (KKVLDARGSNSLPLLR, 127-143 aa). pMyc-SHINC-3 expression vector was transfected into Cos-1 cells. Cell lysate (1 mg of protein) was immunoprecipitated with agarose-conjugated anti-myc antibody (Santa Cruz) and the immunoprecipitates were analyzed by immunoblotting with anti-SHINC-3 antiserum. Myc-tagged SHINC-3 protein was detected as approx. 28 kDa protein.

DETAILED DESCRIPTION OF THE INVENTION

The molecular genetic factors that negate cell death and contribute to tumor growth and metastasis can be attractive targets for therapeutic intervention. In a search for such genes, the present inventors have identified a cDNA fragment encoding a gene which is hereby named as SHINC-3. The SHINC-3 Open Reading Frame is homologous to a recently identified DB83 protein.

SHINC-2 is regulated by Raf protein, which is known to be associated with cancer. Raf-1, the product of the proto-oncogene c-raf-1, is a cytoplasmic 70-75 kDa serine/threonine protein kinase. It plays important roles in cell growth, proliferation, and cell survival (Kolch et al., 1991; Kyriakis et al, 1992; Troppmair et al., 1992; Wang et al., 1996). A variety of biochemical experiments have shown that Raf-1 protein kinase is an important component of the signal transduction pathways initiated by diverse agents, including growth factors, cytokines, ultraviolet radiation, and ionizing radiation (Dent et al., 1992; Devary et al., 1992; Finco et al., 1993; Heidecker et al., 1992; Howe et al., 1992; Kasid et al. 1996; Marshall et al. 1995; Rapp et al., 1991; Suy et al. 1997). In addition, we and others have shown that the constitutive activation of Raf-1 protein kinase occurs by truncation of the regulatory amino terminus and retention of the kinase domain (Heidecker et al., 1990; Kasid et al., 1987; Patel et al., 1997a; Stanton et al., 1989). Activated Raf-1 triggers a kinase cascade that includes the phosphorylation of the mitogen-activated extracellular kinase (MEK), a dual-specificity kinase that stimulates the mitogen-activated protein kinase, MAPK (Kyriakis et al., 1992). Of further importance are observations that activated Raf-1 transactivates transcription from the following sites: AP-1 and Ets binding sites in the polyoma virus enhancer, c-fos and egr-1 promoters, and promoter containing NF-_B binding site (Bruder et al., 1992; Finco et al., 1993; Qureshi et al., 1991; Shengfeng et al., 1993). The role of Raf-1 in the regulation of specific gene expression is unclear.

Depending on the cell type, the constitutive modulation of expression and/or activity of Raf-1 leads to various biological consequences. For example, the catalytic activation of Raf-1 protein kinase is associated with the neoplastic growth recipient fibroblasts and epithelial cells (Stanton et al., 1989; Heidecker et al., 1990; Kasid et al., 1987; Patel et al., 1997). Overexpression or activation of Raf-1 protein kinase is associated with morphologic transformation of immortalized cells (Kolch et al., 1991; Pfeifer et al., 1989) and in vitro radioresistance (Kasid et al., 1993; Pfeifer et al., 1998). Inhibition of endogenous Raf-1 expression via antisense c-raf-1 cDNA transfection has been associated with delayed tumor growth of relatively radioresistant human laryngeal squamous carcinoma-derived cells (SQ-20B) in athymic mice (Kasid et al., 1989). In addition, antisense sequence-specific inhibition of Raf-1 expression causes enhanced radiation sensitivity of SQ-20B cells in culture (Kasid et al., 1989; Soldatenkov et al., 1997).

Combination of antisense raf-1 oligodeoxynucleotide and ionizing radiation treatments caused significant tumor regression compared with single agents in SQ-20B tumor-bearing mice (Gokhale et al., 1999). Other studies have shown that inhibition of Raf-1 expression by antisense raf oligodeoxynucleotides has anti-rumor and radiosensitizing effects in different tumor cell types (Monia et al., 1996; Soldatenkov et al., 1997; Gokhale et al., 1997). A kinase-activated Raf-1 deletion mutant has been shown to improve Bcl-2 mediated resistance to apoptosis, and this-requires targeting of Raf-1 to mitochondrial membranes (Wang et al., 1996). Furthermore, mouse embryos with a targeted disruption of the c-raf-1 gene have been generated and display a phenotype strinkingly similar to that of the epidermal growth factor (EGF) receptor knock-out mice, involving epithelial and placental defects (L. Wojnowski, personal communication). These diverse effects may be at least in part due to the involvement of Raf-1 in the modulation of multiple effectors, each having a more direct role in the specific biological response.

Figure 3:
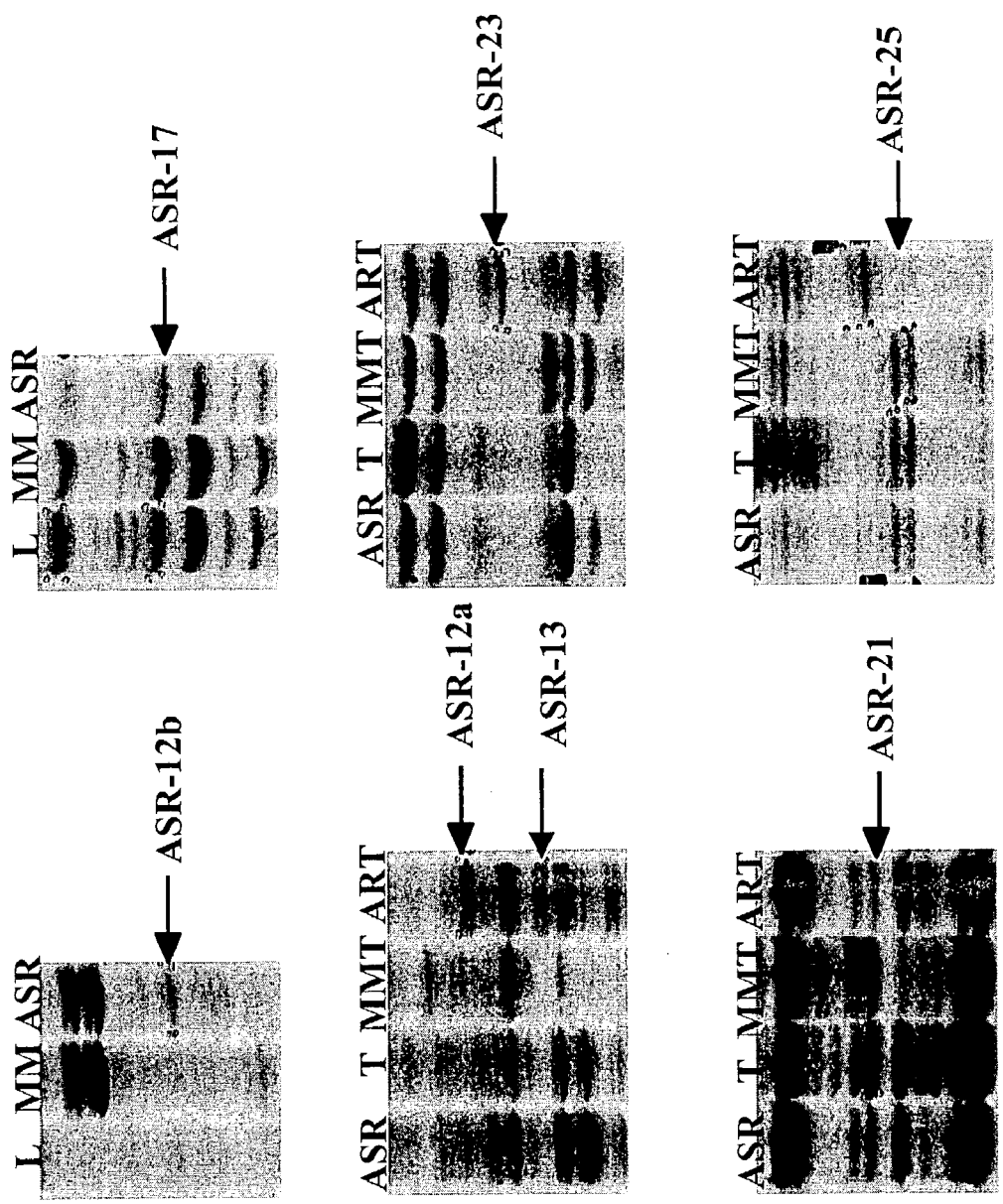
FIG. 3. Identification of differentially expressed mRNAs in DU-145 cells.

The role of Raf-1 in the regulation of specific gene expression is unclear. The power of the differential display of mRNA technology to identify the differentially expressed genes remains undisputed (Liang et al., 1992). It allows the analysis of changes in specific mRNA levels by rapid display and simultaneous expression of mRNAs in the well-matched cell populations (Ligang et al., 1992; Patel et al., 1997). The aim of this study was to identify the differentially expressed genes in the cells treated with antisense c-raf-1 oligonucleotide compared with untreated or mismatch oligonucleotide treated cells (FIG. 3). This study reports novel components of the Raf-1 signaling pathways. BAH, SSRP-1, ODC, ANT, and ALDH10 have been previously implicated in diverse cellular responses including metabolism and cell survival. Our data suggest that expression of these genes may play a role in the Raf-1-mediated biological activity of DU-145 and MDA-MB231 cells. Further investigations are necessary to determine role of SHINC-2 and SHINC-3 in the cellular response. Identification of specific targets may provide useful markers for prognosis and therapy selection in prostate and breast cancer.

Raf-1, a cytoplasmic serine/threonine protein kinase, plays an important role in mitogen- and damage-responsive cellular signal transduction pathways. Differential-display of mRNA was used to identify the genes differentially expressed in human prostate cancer cells (DU-145) treated with antisense raf oligonucleotide. Seven differentially expressed cDNA fragments were identified and sequenced. Northern blot analysis revealed that human aspartyl p-hydroxylase (BAH), human structure specific recognition protein-1 (SSRP-1), human mitochondrial oxodicarboxylate carrier (OXDC), human mitochondrial ADP/ATP translocase (ANT), human fatty aldehyde dehydrogenase (ALDH10), and two as-yet unidentified cDNAs (SHINC-2 and SHINC-3) were down-regulated in DU-145 cells and MDA-MB231 cells treated with antisense raf-1 oligonucleotide. The SHINC-2 (347 bp partial sequence and 2626 bp complete sequence) and SHINC-3 (191 bp) cDNA did not show significant matches with sequences in any DNA databases, and these may represent novel genes. The SHINC-2 transcripts, ~2.5 kb and ~3.5 kb, were observed in most human tissues and human cancer cell types, indicating its housekeeping function. SHINC-3 transcripts, ~8.0 kb, ~4.0 kb and ~2.5 kb, were observed in prostate and testis, indicating tissues specificity. This study reports novel components of the Raf-1 signaling pathways, BAH, SSRP-1, OXDC, ANT, and ALDH10 have been previously implicated in diverse cellular responses including metabolism and cell survival. Our data suggest that expression of these genes may play a role in the Raf-1-mediated biological activity of DU-145 cells and MDA-MB231 cells. Further investigations are necessary to determine role of SHINC-2 and SHINC-3 in the cellular response. Identification of specific-targets may provide useful markers for prognosis and therapy selection in prostate and breast cancer.

The serine/threonine protein kinase Raf-1 responds to diverse stimuli and has been implicated in a number of biological responses. A global view of the molecular events following the modulation of Raf-1 is important in the understanding of this otherwise very complex regulatory process. Our strategy to identify the components of the Raf-1 signaling pathway was based on the premise that biological changes associated with the constitutive modification of Raf-1 protein kinase expression or activity are related to the modifications of the specific gene expression. Using well-characterized human prostate cancer cells or breast cancer cells, we demonstrate that a increase in the steady-state mRNA levels of SSRP-1 and a decrease in that of BAH, OXDC, ANT, ALDH10, SHINC-2 and SHINC-3 correlates with the downregulation of Raf-1 protein kinase. None of these sequences has been recognized as part of the Raf-1 signaling pathway thus far.

BAH specifically hydroxylates one Asp or Asn residue in certain proteins. Functional role for aspartyl β-hydroxylation of proteins has not been defined (Rees et al., 1985; Sunnerhagen et al., 1993). The aspartyl β-hydroxylase (BAH) hydroxylation consensus sequence is contained within calcium-binding epithelial growth factor domains that are found in proteins of diverse function. Consensus sequence domains contain the amino acids Asp, Asp/Asn, Asp/Asn, and Tyr/Phe at defined positions. The alignment of these latter four residues are thought to signal post-translational hydroxylation of the third site in the consensus by BAH (Davis, 1990). The consensus sequence for aspartyl p-hydroxylation has been identified in a diverse group of proteins including clotting factors (Stenflo et al., 1991), Notch receptors and ligands (Rebay et al., 1991; Sun et al., 1998; Nakamura et al., 1999), in structural proteins of the extracellular matrix (Dowing et al., 1996), and in ligands of the tyro-3/Ax1 family of receptor tyrosine kinase (Goruppi et al., 1997). A 4.3-kb cDNA isolated from human osteosarcoma cDNA expression library led to observations of two transcripts (2.6 and 4.3 kb) in a Northern blot analysis of human tissues (Korioth et al., 2000). Human junctin which has a completely matched region to human BAH was present both in cardiac and skeletal muscle, and the sizes of the transcripts were approximately 3.0 and 4.2 kb (Lim et al., 2000) The other report showed three transcripts (2.8, 4.5 and 5.2 kb) in human A549 cells (Dinchuk et al., 2000). We found three transcripts (2.8 kb, 4.5 kb and 5.2 kb) in DU-145 cells and some human tissues and human cancer cell lines (FIG. 5A).

SSRP-1 is 81-kDa protein containing several highly charged domains and a stretch of 75 amino acids 47% identical to a protion of the highly mobility group (HMG) protein HMG1. SSRP-1 mRNA has 2.8 kb and expressed in brain, heart, ileum, jejunum, kidney, liver muscle, spleen, some bladder and testicular cell lines (Bruhn, et al., 1992). SSRP-1 binds specifically to DNA modified with cisplatin, an anticancer drug which-binds bind to DNA (Bruhn, et al., 1992).

Mitochondrial oxodicarboxylate carrier transports C5-C7 oxodicarboxylates across the inner membranes of mitochondria and members of the family of mitochondrial carrier proteins. Human OXDC cDNA was isolated and sequenced, containing 2024 nucleotides (Fiermonte et al., 2001). Three transcripts were shown by northern blot analysis in DU-145 cells. 2.0 kb transcript is the most abundant among three transcripts, but no change in expression level (FIG. 5A). We are not sure the other two transcripts are isoforms of OXDC.

ANT proteins catalyze the exchange of mitochondrial ATP for cytosolic ADP, and in doing so play a key role in maintaining cellular homeostasis (Luciakova et al., 2000). ANTs are encoded by three genes in both mammals (Cozens et al., 1989; Houldsworth et al. 1988; Neckelmann et al., 1987;) and yeast (Lawson et al., 1988; Kolarov et al., 1990). In mammals, these genes are expressed in tissue- and developmentally specific manners, and they appear to play a central role in initiation of apoptosis via the mitochondrial pathway (Marzo et al., 1998; Green et al., 1998). By northern blot analysis, expression of two transcripts (4.0 kb and 1.3 kb) were seen in DU-145 cells. 1.3 kb transcript corresponds to the known size (Houldsworth et al., 1988), but 4.0 kb transcripts has not reported yet.

Aldehyde dehydrogenases (ALDHs) compose a group of isozymes with the general role of catalyzing the oxidation of a wide variety of aldehydes to their corresponding carboxylic acids (Rogers et al., 1997). They are widely distributed in most mammalian tissues, and some of them are inducible by various compounds or by carcinogenesis (Limdahl et al., 1992; Yoshida et al., 1992) Fatty aldehyde dehydrogenase (ALDH10/FALDH), a component of the fatty alcohol: NAD+ oxidoreductase complex, catalyzes the oxidation of saturated or unsaturated aliphatic aldehydes of medium- or long-chain length to fatty acids (Kelson et al., 1997). ALDH10 (FALDH) is widely expressed as three transcripts of 2.0, 3.8 and 4.0 kb, which originate from multiple polyadenylation signals in the 3' UTR (Rogers et al., 1997).

Down-regulation of ALDH10 in As-raf ODN treated cells may reflect decrease of fatty acid synthesis. We found the 4.0 kb-transcript of BAH in DU-145 cells by Northern blot analysis, which matched to the known size (FIG. 5A).

The two as-yet unidentified genes, SHINC-2 and SHINC-3 were down-regulated in the As-raf ODN treated cells, which suggests that these molecules are novel effectors of the Raf-1 pathway. SHINC-2 expression in multiple tissue and cancer cell lines indicates the possible housekeeping function, SHINC-3 expression indicates the tissue specific function. The isolation of their full-length cDNAs is necessary to assess the biological significance of these genes in human prostate cancer and breast cancer cells.

In this report, we identified six (seven) novel components of the Raf-1-mediated signaling pathway. While the precise mechanism of induction of the specific gene expression remains to be studied, processing, and/or stability of several mRNAs, resulting in the differential expression of multiple factors. Identification of these distinct effectors also implies that Raf-1 may function via multiple pathways, which could be selectively utilized in different cell types.

Based on these discoveries, the present invention relates to a novel gene, SHINC-3, the expression of which is increased by agents which mediate apoptosis, the corresponding polypeptide, and application thereof in diagnostic and therapeutic methods. Particularly, the invention provides a novel target for identifying compounds that promote apoptosis in certain of cancers and promote cell proliferation growth in other cells.

As noted, the invention is broadly directed to a novel gene referred to as SHINC-3. Reference to SHINC-3 herein is intended to be construed to include SHINC-3 proteins of any origin which are substantially homologous to and which are biologically equivalent to the SHINC-3 characterized and described herein. Such substantially homologous SHINC-3 may be native to any tissue or species and, similarly, biological activity can be characterized in any of a number of biological assay systems.

The term "biologically equivalent" is intended to mean that the compositions of the present invention are capable of demonstrating some or all of the same biological properties in a similar fashion, not necessarily to the same degree as the SHINC-3 gene and protein isolated as described herein or recombinantly produced human SHINC-3 of the invention.

By "substantially homologous" it is meant that the degree of homology of human SHINC-3 from any species is greater than that between SHINC-3 and any previously reported apoptopic modulating gene. Also included within the meaning of substantially homologous is any SHINC-3 which may be isolated by virtue of cross-reactivity with antibodies to the SHINC-3 described herein or whose encoding nucleotide sequences including genomic DNA, mRNA or cDNA may be isolated through hybridization with the complementary sequence of genomic or subgenomic nucleotide sequences or cDNA of the SHINC-3 herein or fragments thereof. It will also be appreciated by one skilled in the art that degenerate DNA sequences can encode human SHINC-3 and these are also intended to be included, within the present invention as are allelic variants of SHINC-3.

Preferred SHINC-3 of the present invention have been identified and isolated in purified form as described. Also preferred is SHINC-3 prepared by recombinant DNA technology. By "pure form" or "purified form" or "substantially purified form" it is meant that a SHINC-3 composition is substantially free of other proteins which are not SHINC-3.

Sequence identity or percent identity is intended to mean the percentage of same residues between two sequences, wherein the two sequences are aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3, window value in pairwise alignment=5; diagonals saved in pairwise alignmentz=5. The residue weight table used for the alignment program is PAM25O (Dayhoffet al., in Atlas of Protein Sequence and Structure, Dayhoff, Ed., NDRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to human SHINC-3 when determining percent conservation with non-human SHINC-3, and referenced to SHINC-3 when determining percent conservation with non-SHINC-3 proteins. Conservative amino acid changes satisfying this requirement are: R-K; E-D, Y-F, L-M; V-I, Q-H.

In one aspect, the invention provides a SHINC-3 polynucleotide that encodes the mature SHINC-3 protein or a fragment or variant thereof. Pursuant to the invention, the SHINC-3 polynucleotide is a nucleic acid molecule that comprises, consists of, or consists essentially of a sequence of nucleotides from the nucleic acid sequence of SEQ ID NO: 2. For example, a SHINC-3 polynucleotide can be or comprise a sequence of nucleotides 1 to about 2684 of SEQ ID NO: 2, such as from nucleotides 2 to about 2684 of SEQ ID NO: 2. Desirably, the SHINC-3 polynucleotide contains from about 10 to about 2684 contiguous nucleotides from the nucleic acid sequence of SEQ ID NO: 2, such as from about 10 to about 300 contiguous nucleotides (e.g., from about 50 to about 200 contiguous nucleotides) from the nucleic acid sequence of SEQ ID NO: 2 or from about 100 to about 400 contiguous nucleotides from the nucleic acid sequence of SEQ ID NO: 2, such as from about 100 to about 300 contiguous nucleotides from the nucleic acid sequence of SEQ ID NO: 2. Other non-limiting examples of a SHINC-3 polynucleotide can be or comprise a nucleic acid sequence from about 1 to about 191 of SEQ ID NO: 1, such as from about 2 to about 191 of SEQ ID NO: 1. For example, a SHINC-3 polynucleotide can have from about 10 to about 191 contiguous nucleatides from the nucleic acid sequence of SEQ ID NO: 1, such as from about 50 to about 100 contiguous nucleotides from the nucleic acid sequence of SEQ ID NO: 1 or from about 10 to about 175 contiguous nucleotides or from about 100 to about 180 contiguous nucleotides from the nucleic acid sequence of SEQ ID NO: 1.

In certain circumstances, it may be desirable to modulate or decrease the amount of SHINC-3 expressed. Thus, in another aspect of the present invention, SHINC-3 anti-sense oligonucleotides can be made and a method utilized for diminishing the level of expression of SHINC-3 by a cell comprising administering one or more SHINC-3 anti-sense oligonucleotides. By SHINC-3 anti-sense oligonucleotides reference is made to oligonucleotides that have a nucleotide sequence that interacts through base pairing with a specific complementary nucleic acid sequence involved in the expression of SHINC-3 such that the expression of SHINC-3 is reduced. Preferably, the specific nucleic acid sequence involved in the expression of SHINC-3 is a genomic DNA molecule or mRNA molecule that encodes SHINC-3. This genomic DNA molecule can comprise regulatory regions of the SHINC-3 gene, or the coding sequence for mature SHINC-3 protein.

Thus, the SHINC-3 polynucleotide can be or comprise (or consist essentially of) a sequence complementary (e.g., antisense) to the SHINC-3 coding sequence or a portion thereof. The term complementary to a nucleotide sequence in the context of antisense SHINC-3 polynucleotides and methods therefor means sufficiently complementary to such a sequence as to allow hybridization to that sequence in a cell, i.e., under physiological conditions. The antisense SHINC-3 polynucleotide typically bind at least five nucleotides of SHINC-3 DNA, and preferably comprise a sequence containing from about 8 to about 50 or to about 100 nucleotides (e.g., from about 10 to about 30 nucleotides), and more preferably the antisense SHINC-3 polynucleotide comprise from about 15 to about 25 nucleotides and can hybridize to a portion of the SHINC-3 transcript to inhibit SHINC-3 expression within a cell. While such an antisense SHINC-3 polynucleotide can be an exact complement to a portion of SEQ ID NO 1 or 2, it need not be, so long as it can effectively inhibit expression.

The antisense SHINC-3 polynucleotide can have a sequence consisting essentially of a complement to a portion of SEQ ID NO:2 (see FIG. 7), or consisting of a complement to a portion of SEQ ID NO:2. The antisense SHINC-3 polynucleotide can also contain a variety of modifications that confer resistance to nucleolytic degradation such as, for example, modified internucleoside linages (Uhlmann and Peyman, Chemical Reviews 90:543-548 1990; Schneider and Banner, Tetrahedron Lett. 37:335, 1990 which are incorporated by reference), modified nucleic acid bases as disclosed in U.S. Pat. No. 5,958,773 and patents disclosed therein, and/or sugars and the like.

Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773. The antisense compounds of the invention can include modified bases. The antisense SHINC-3 poly nucleotide of the invention can also be modified by chemically linking the antisense SHINC-3 polynucleotide to one or more moieties or conjugates to enhance the activity, cellular distribution, or cellular uptake of the antisense SHINC-3 polynucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565, 552, 5,567,810, 5,574,142, 5,585,481, 5,587,371, 5,597,696 and 5,958,773.

Chimeric antisense SHINC-3 polynucleotide are also within the scope of the invention, and can be prepared from the present inventive antisense SHINC-3 polynucleotide using the methods described in, for example, U.S. Pat. Nos. 5,013,830, 5,149,797, 5,403,711, 5,491,133, 5,565,350, 5,652,355, 5,700,922 and 5,958,773.

In the antisense art, a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. mRNA levels in the cell can be measured routinely in treated and control cells by reverse transcription of the mRNA and assaying the cDNA levels. The biological effect can be determined routinely by measuring cell growth, proliferation or viability as is known in the art. Assays for measuring apoptosis are also known.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A. D., T.I.B.S. 23:45-50, 1998.).

In another embodiment, the SHINC-3 nucleotide can be a ribozyme or siRNA (or RNAi) containing a portion complementary to the SHINC-3 sequence. In this regard, 21 or 22 nucleotide double stranded RNAs with 2-nucleotide 3' overhangs have been reported to show RNA-interference gene suppression activity in mammalian cells (see, e.g., Elbashir et al., Nature 411, 494-98 (2001) and Caplen et al., Proc. Natl. Acad. Sci. USA 98, 9742-47 (2001)).

The SHINC-3 polynucleotide sequence (including a antisense SHINC-3 polynucleotide) can contain some variation from the exemplary sequences, so long as it encodes a SHINC-3 protein with biological activity or hybridizes with sufficient stringency to be used as an antisense nucleotide or a probe. In this regard, the SHINC-3 polynucleotide can be at least 85% identical or complementary to all or a portion of SEQ ID NOs:1 or 2, and more preferably is at least about 90% identical or complementary to one of these exemplary sequences or a fragment thereof (e.g., at least about 95% identical or complementary to all or a portion of SEQ ID NOs:1 or 2).

Typically, homologous polynucleotide sequences can be confirmed by hybridization under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each, homologous sequences can be identified which contain at most about 25-30% basepair mismatches. More preferably, homologous nucleic acid strands contain 15-25% basepair mismatches, even more preferably 5-15% basepair mismatches.

The polynuceotide of the present invention can be of any chemical type (e.g., DNA, RNA, etc.). However, preferably the SHINC-3 polynucleotide (including coding SHINC-3 nucleotides or antisense (e.g., complementary) SHINC-3 nucleotides) is DNA. The inventive SHINC-3 polynucleotide can be made using any desired method. For example, the desired polynucleotide can be produced using recombinant techniques, such as by cloning from a library, dgestion of a desired fragment, etc. Alternatively, routine synthetic machinery (e.g., solid state devices) can be employed to synthesize the desired SHINC-3 polynucleotide.

The SHINC-3 polynucleotide can be used as a probes that can be used to detect complementary nucleotide sequences, for example, in hybridization protocols such as Northern or Southern blotting or in situ hybridizations. Polynucleotide probes of the invention comprise or consist essentially of at least 12, 13, 14, 15, 16, 17, 18, 19, 20, 30, or 40 or more contiguous nucleotides of the sequence contained in FIG. 4 or 7 (SEQ ID Nos: 1 or 2). By "consisting essentially of" in this context it is understood that the sequence of the probe can contain minor variants from the complementary sequence, so long as it is able to hybridize suitably for use as a probe. Polynucleotide probes of the invention can comprise a detectable label, such as a radioisotopic, fluorescent, enzymatic, or chemiluminescent label.

Isolated genes corresponding to the polynucleotide sequences disclosed herein are also provided. Standard molecular biology methods can be used to isolate the corresponding genes using the cDNA sequences provided herein. These methods include preparation of probes or primers from the nucleotide sequence shown in FIG. 4 or 7 (SEQ ID Nos: 1 or 2) for use in identifying or amplifying the genes from mammalian, including human, genomic libraries or other sources of human genomic DNA.

Polynucleotide molecules of the invention can also be used as primers to obtain additional copies of the polynucleotides, using polynucleotide amplification methods. Polynucleotide molecules can be propagated in vectors and cell lines using techniques well known in the art. Polynucleotide molecules can be on linear or circular molecules. They can be on autonomously replicating molecules or on molecules without replication sequences. They can be regulated by their own or by other regulatory sequences, as is known in the art.

Polynucleotide molecules comprising the coding sequences disclosed herein can be used in a polynucleotide construct, such as a DNA or RNA construct. Polynucleotide molecules of the invention can be used, for example, in an expression construct (e.g., an expression vector) to express all or a portion of a protein, variant, fusion protein, or single-chain antibody in a host cell. Accordingly, the invention provides a vector that comprises a SHINC-3 polynucleotitide (e.g., a SHINC-3 coding polynucleotide or a SHINC-3 antisense polynucleotide) An expression construct comprises a promoter that is functional in a chosen host cell. The skilled artisan can readily select an appropriate promoter from the large number of cell type-specific promoters known and used in the art. The expression construct can also contain a transcription terminator, which is functional in the host cell. The expression construct comprises a polynucleotide segment that encodes all or a portion of the desired protein. The polynucleotide segment is located downstream from the promoter and in operable linkage thereto. Transcription of the polynucleotide segment initiates at the promoter. The expression construct can be linear or circular and can contain sequences, if desired, for autonomous replication.

However, produced, the expression construct containing a SHINC-3-encoding sequence can be engineered into a suitable vector for expression in a desired hoist cell system. The expression cassette must be introduced into the cells in a manner suitable for them to express the SHINC-3 polynucleotide contained therein. Any suitable vector can be so employed, many of which are known in the art. Examples of such vectors include naked DNA vectors (such as oligonucleotides or plasmids), viral vectors such as adeno-associated viral vectors (Berns et al., Ann. N.Y. Acad. Sci., 772, 95-104 (1995)), adenoviral vectors (Bain et al., Gene Therapy, 1, S68 (1994)), herpesvirus vectors (Fink et al., Ann. Rev. Neurosci., 19, 265-87 (1996)), packaged amplicons (Federoff et al., Proc. Nat. Acad. Sci. USA, 89, 1636-40 (1992)), pappiloma virus vectors, picornavirus vectors, polyoma virus vectors, retroviral vectors, SV40 viral vectors, vaccinia virus vectors, and other vectors. In addition to the expression cassette of interest, the vector can also include other genetic elements, such as, for example, genes encoding a selectable marker (e.g., b-gal or a marker conferring resistance to a toxin), a pharmacologically active protein, a transcription factor, or other biologically active substance.

Once a given type of vector is selected, its genome must be manipulated for use as a background vector, after which it must be engineered to incorporate exogenous polynucleotides. Methods for manipulating the genomes of vectors are well known in the art (see, e.g., Sambrook et al., supra) and include direct cloning, site specific recombination using recombinases, homologous recombination, and other suitable methods of constructing a recombinant vector. In this manner, the expression cassette can be inserted into any desirable position of the vector.

Expression of an endogenous gene encoding a protein of the invention can also be manipulated by introducing by homologous recombination a DNA construct comprising a transcription unit in frame with the endogenous gene, to form a homologously recombinant cell comprising the transcription unit. The transcription unit comprises a targeting sequence, a regulatory sequence, an exon, and an unpaired splice donor site. The new transcription unit can be used to turn the endogenous gene on or off as desired. This method of affecting endogenous gene expression is taught in U.S. Pat. No. 5,641,670. The targeting sequence is a segment of at least 10, 12, 15, 20, or 50 contiguous nucleotides from the nucleotide sequence shown in FIG. 7 (SEQ ID NO 2). The transcription unit is located upstream to a coding sequence of the endogenous gene. The exogenous regulatory sequence directs transcription of the coding sequence of the endogenous gene.

A vector harboring the SHINC-3 expression construct can be introduced into the cells by any means appropriate for the vector employed. Many such methods are well-known in the art (Sambrook et al., supra; see also Watson et al., Recombinant DNA, Chapter 12, 2d edition, Scientific American Books (1992)). Thus, plasmids are transferred by methods such as calcium phosphate precipitation, electroporation, liposome-mediated transfection, gene gun, microinjection, viral capsid-mediated transfer, polybrene-mediated transfer, protoplast fusion, etc. Viral vectors are best transferred into the cells by infecting them; however, the mode of infection can vary depending on the virus.

Cells into which the SHINC-3 expression vector has been transferred can be used in the inventive method as transient transformants. Alternatively, where the cells are cells in vitro, they can be subjected to several rounds of clonal selection (if the vector also contains a gene encoding a selectable marker, such as a gene conferring resistance to a toxin) to select for stable transformants. Within the cells, the SHINC-3 expression construct is expressed. Successful expression of the gene can be assessed via standard molecular biological techniques (e.g., Northern hybridization, Western blotting, immunoprecipitation, enzyme immunoassay, etc.).

The host cell comprising the expression construct can be any suitable prokaryotic or eukaryotic cell. Expression systems in bacteria include those described in Chang et al., Nature (1978) 275: 615; Goeddel et al, Nature (1979) 281: 544; Goeddel et al, Nucleic Acids Res. (1980) 5:4057; EP 36,776; U.S. Pat. No. 4,551,433; deBoer et al, Proc. Natl. Acad Sci. USA (1983) 80: 21-25; and Siebenlist et al, Cell (1980) 20: 269.

Expression systems in yeast include those described in Hinnen et al, Proc. Natl Acad. Sci. USA (1978) 75: 1929; Ito et al, J Bacterial (1983) 153: 163; Kurtz et al, Mol Cell Biol (1986) 6: 142; Kunze et al, J Basic Microbiol (1985) 25: 141; Gleeson et al, J. Gen. Microbiol. (1986) 132: 3459, Roggenkamp et al, Mol Gen. Genet. (1986) 202: 302; Das et al, J Bacteriol. (1984) 755: 1165; De Louvencourt et al., J Bacteriol (1983) 754: 737, Van den Berg et al., Bio/Technology (1990) 8: 135; Kunze et al., J. Basic Microbiol (1985) 25: 141; Gregg et al., Mol. Cell. Biol. (1985) 5: 3376; U.S. Pat. No. 4,837,148; U.S. Pat. No. 4,929,555; Beach and Nurse, Nature (1981) 300: 706; Davidow et al, Curr. Genet. (1985) Ip: 380; Gaillardin et al, Curr. Genet. (1985) 10: 49; Ballance et al., Biochem. Biophys. Res. Commun. (1983) 112: 284-289; Tilburn et al., Gene (1983) 26: 205-22; Yelton et al., Proc. Natl. Acad, Sci. USA (1984) 81: 1470-1474; Kelly and Hynes, EMBO J. (1985) 4: 475-479; EP 244,234; and WO 91/00357.

Expression of heterologous genes in insects can be accomplished as described in U.S. Pat. No. 4,745,051; Friesen et al. (1986) "The Regulation of Baculoviras Gene Expression" in: THE MOLECULAR BIOLOGY OF BACULOVIRUSES (W. Doerfler, ed.); EP 127,839; EP 155,476; Vlak et al., J. Gen. Virol (1988) 69: 765-776; Miller et al, Ann. Rev. Microbiol (1988) 42: 177; Carbonell et al, Gene (1988) 73: 409; Maeda et al., Nature (1985) 315: 592-594; Lebacq-Verheyden et al., Mol. Cell Biol. (1988) 8: 3129; Smith et al., Proc. Natl. Acad. Sci. USA (1985) 82: 8404; Miyajima et al., Gene (1987) 58: 273; and Martin et al., DNA (1988) 7: 99. Numerous baculoviral strains and variants and corresponding permissive insect host cells from hosts are described in Luckow et al., Bio/Technology (1988) 6: 47-55, Miller et al., in GENERIC ENGINEERING (Setlow, J. K. et al eds.), Vol. 8 (Plenum Publishing, 1986), pp. 277-279; and Maeda et al., Nature, (1985) 315: 592-594.

Mammalian expression can be accomplished as described in Dijkema et al, EMBO J. (1985) 4: 761; Gormanetal, Proc. Natl. Acad. Sci. USA (1982b) 79: 6777; Boshart et al., Cell (1985) 41: 521; and U.S. Pat. No. 4,399,216. Other features of mammalian expression can be facilitated as described in Ham and Wallace, Meth Enz. (1979) 58: 44; Barnes and Sato, Anal. Biochem. (1980) 102: 255; U.S. Pat. No. 4,767,704; U.S. Pat. No. 4,657,866; U.S. Pat. No. 4,927,762; U.S. Pat. No. 4,560,655; WO 90/103430, WO 87/00195, and U.S. RE 30,985.

Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Regardless of how they are produced, the invention further provides a host cell that includes a vector, as disclosed above, that contains an expression construct encoding a SHINC-3 polypeptide. The recombinant cell can be of any desired type, including insect, yeast, or mammalian cells (e.g., immortalized cells, culture cells, cells in vivo, etc.).

The recombinant host cell harboring the SHINC-3 expression construct, in turn, can be employed to produce SHINC-3 polypeptide. In this respect, the host cell (or a population of host cells) harboring the SHINC-3 expression construct can be cultured under conditions favorable to the expression of the SHINC-3 expression construct within the cell. It is within the ordinary skill of the art to select suitable culture conditions for expression of transgenes within cell types, the precice consitions varying according to the type of cell, the nature of the expression construct, and other factors known to those of ordinary skill in the field. Thus cultured, the host cell(s) produce the SHINC-3 protein, from which it can be recovered. The SHINC-3 polypeptide can be recovered from cells in which it accumulates internatlly, for example, by lysis of the cells and subsequent purification (e.g., using column separeation, immunohistochemical techniques, or other suitable method). Alternatively, where the SHINC-3 polypeptide is produced as a secreted protein, it can be recovered from the supernatant culture medium.

The coding sequence (or expression constructs) disclosed herein can also be used to construct transgenic animals, such as cows, goats, pigs, or sheep. Female transgenic animals can then produce proteins, polypeptides, or fusion proteins of the invention in their milk. Methods for constructing such animals are known and widely used in the art.

In another aspect, the invention provides a SHINC-3 polypeptide. In this respect, the SHINC-3 polypeptide can be, comprise, or consist essentially of a full length SHINC-3 protein, for example as encoded by the nucleic acid of SEQ ID NO:2. An example of such a polypeptide is SEQ ID NO:3, depicted in FIG. 7, fragments thereof are included within the scope of the present invention. However, in other embodiments, the SHINC-3 polypeptide can be or comprise a polypeptide fragment, homolog, anlog, or fusion protein of SHINC-3. For example, SHINC-3 polypeptide fragments of the invention can comprise at least 8, 10, 12, 15, 18, 19, 20, 25, 50, 75, 100, or 108 (e.g., at least 200) contiguous amino acids of an amino acid sequence encoded by a nucleic acid sequence comprising the sequence contained in FIG. 7 (SEQ ID NO 2) or of the amino acid sequence of SEQ ID NO:3. Also included are all intermediate length fragments in this range, such as 51, 52, 53, etc.; 70, 71, 72, etc.; and 100, 101, 102, etc., which are exemplary only and not limiting.

Preferred SHINC-3 polypeptides that can be shorter than the full-length SHINC-3 protein include epitope-bearing portions of the polypeptide encoded by a nucleic acid sequence comprising SEQ ID NO:2. For example, the epitope-bearing portion can include from about 5 to about 30 amino acids encoded by contiguous nucleic acids of SEQ ID NO:2, such as from about 10 to about 15 amino acids encoded by contiguous nucleic acids of SEQ ID NO:2. An exemplary epitope-bearing portion of SEQ ID NO:2 is a SHINC-3 polypeptide having the sequence of SEQ ID NO:4. An epitope-bearing SHINC-3 fragment can be used to raise antibodies that can selectively bind to the mature SHINC-3 protein.

A SHINC-3 protein of the present invention also can be or comprise a variant of the SHINC-3 polypeptide disclosed herein. Variants can be naturally or non-naturally occurring. Naturally occurring variants are found in humans or other species and comprise amino acid sequences which are substantially identical to the amino acid sequence shown in FIG. 7 (SEQ ID NO 3). Species homologs of the protein can be obtained using subgenomic polynucleotides of the invention, as described below, to make suitable probes or primers to screening cDNA expression libraries from other species, such as mice, monkeys, yeast, or bacteria, identifying cDNAs which encode homo logs of the protein, and expressing the cDNAs as is known in the art. Desirably, the SHINC-3 variants of the present invention retain the biological activity of native SHINC-3 in that the protein modulates cancer cell proliferation and/or apoptosis, although not necessarily at the same level of potency as that of the native full-length SHINC-3 protein.

Non-naturally occurring variants which retain substantially the same biological activities as naturally occurring SHINC-3 protein variants are also included here. Preferably, naturally or non-naturally occurring variants have amino acid sequences which are at least 85%, 90%, or 95% identical to the amino acid sequence encoded by a nucleic acid sequence comprising the sequence shown in FIG. 7 (SEQ ID NO 2) or of the amino acid sequence of SEQ ID NO:3. More preferably, the molecules are at least 96%, 97%, 98% or 99% identical. The SHINC-3 polypeptide can be highly identical to the full-length SHINC-3 protein or to a portion thereto. For example, the SHINC-3 protein can be at least 85%, 90%, or 95% identical to amino acids encoded by at least 100 contiguous nucleic acids from SEQ ID NO:2, such as at least 200 contiguous nucleic acids from SEQ ID NO:2. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482-489.

Guidance in determining which amino acid residues can be substituted, inserted, or deleted without abolishing biological or immunological activity can be found using computer programs well known in the art, such as DNASTAR software. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

A subset of mutants, called muteins, is a group of polypeptides in which neutral amino acids, such as serines, are substituted for cysteine residues which do not participate in disulfide bonds. These mutants may be stable over a broader temperature range than native secreted proteins. See Mark et al., U.S. Pat. No. 4,959,314. The inventve SHINC-3 polypeptide includes such muteins, as well as other variants.

It is reasonable to expect that an isolated replacement of a leucine with an isoleucine or valine, an aspartate with a glutamate, a threonine with a serine, or a, similar replacement of an amino acid with a structurally related amino acid will not have a major effect on the biological properties of the resulting secreted protein or polypeptide variant. Properties and functions of SHINC-3 polypeptide (including variants) are of the same type as a protein comprising the amino acid sequence encoded by a nucleic acid sequence comprising the nucleotide sequence shown in FIG. 7 (SEQ ID NO 2) or of the amino acid sequence of SEQ ID NO:3, although the properties and functions of variants can differ in degree.

SHINC-3 polypeptide variants of the present invention also include glycosylated forms, aggregative conjugates with other molecules, and covalent conjugates with unrelated chemical moieties. SHINC-3 polypeptide variants also include allelic variants, species variants, and muteins. Truncations or deletions of regions which do not affect the differential expression of the SHINC-3-protein gene are also variants. Covalent variants can be prepared by linking functionalities to groups which are found in the amino acid chain or at the N- or C-terminal residue, as is known in the art.

The invention further includes variations of the SHINC-3 polypeptide which show comparable expression patterns or which include antigenic regions. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Of particular interest are substitutions of charged amino acids with another charged amino acid and with neutral or negatively charged ammo acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967), Robbins et al., *Diabetes* 35:838-845 (1987); Cleland et al., *Crit. Rev. Therapeutic Drug Carrier Systems* 10:307-371 (1993)).

It will be recognized in the art that some amino acid sequence of the SHINC-3 polypeptide of the invention can be varied without significant effect on the structure or function of the protein. If such differences in sequence are contemplated, it should be remembered that there are areas on the protein that determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the SHINC-3 polypeptides of the present invention may include one or more amino acid substitutions, deletions or additions, either from natural mutations or human manipulation.

Amino acids in the inventive SHINC-3 polypeptide that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J Mol. Biol.* 224:899-904 (1992) and de Vos et al. *Science* 255:306-312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

Fusion proteins comprising proteins or polypeptide fragments of SHINC-3 can also be constructed. Fusion proteins are useful for generating antibodies against amino acid sequences and for use in various assay systems. For example, fusion proteins can be used to identify proteins which interact with a protein of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence and/or a transmembrane domain of SHINC-3 or a fragment thereof can be used to target other protein domains to cellular locations in which the domains are not normally found, such as bound to a cellular membrane or secreted extracellularly.

A fusion protein comprises two protein segments fused together by means of a peptide bond. Amino acid sequences for use in fusion proteins of the invention can utilize an amino acid sequence encoded by a nucleic acid sequence comprising the sequence shown in FIG. 7 (SEQ ID NO 2) or can be prepared from biologically active variants such as those described above. The first protein segment can consist of a full-length SHINC-3 or a portion thereof.

Other first protein segments can consist of at least 8, 10, 12, 15, 18, 19, 20, 25, 50, 75, 100, 108 contiguous amino acids selected from SEQ ID NO:3 or the sequence encoded by the nucleic acid sequence shown in FIG. 7 (SEQ ID NO 2). The contiguous amino acids listed herein are not limiting and also include all intermediate lengths such as 20, 21, 22, etc.; 70, 71, 72, etc.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP 16 protein fusions.

These fusions can be made, for example, by covalently linking two protein segments or by standard procedures in the art of molecular biology. Recombinant DNA methods can be used to prepare fusion proteins, for example, by making a DNA construct which comprises a coding sequence comprising the sequence contained in FIG. 7 (SEQ ID NO 2) in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Proteins, fusion proteins, or polypeptides of the invention can be produced by recombinant DNA methods, as noted above. For production of recombinant proteins, fusion proteins, or polypeptides, a coding sequence of the nucleotide sequence comprising the sequence shown in FIG. 7 (SEQ ID NO 2) can be expressed in prokaryotic or eukaryotic host cells using expression systems known in the art. These expression systems include bacterial, yeast, insect, and mammalian cells. The resulting expressed protein can then be purified from the culture medium or from extracts of the cultured cells using purification procedures known in the art. For example, for proteins fully secreted into the culture medium, cell-free medium can be diluted with sodium acetate and contacted with a cation exchange resin, followed by hydrophobic interaction chromatography. Using this method, the desired protein or polypeptide is typically greater than 95% pure. Further purification can be undertaken, using, for example, any of the techniques listed above.

It may be necessary to modify a protein produced in yeast or bacteria, for example by phosphorylation or glycosylation of the appropriate sites, in order to obtain a functional protein. Such covalent attachments can be made using known chemical or enzymatic methods. SHINC-3 protein or polypeptide of the invention can also be expressed in cultured host cells in a form that will facilitate purification. For example, a protein or polypeptide can be expressed as a fusion protein comprising, for example, maltose binding protein, glutathione-S-transferase, or thioredoxin, and purified using a commercially available kit. Kits for expression and purification of such fusion proteins are available from companies such as New England BioLabs, Pharmacia, and Invitrogen. Proteins, fusion proteins, or polypeptides can also be tagged with an epitope, such as a "Flag" epitope (Kodak), and purified using an antibody that specifically binds to that epitope.

As an alternative to recombinant production, synthetic chemical methods, such as solid phase peptide synthesis, can be used to synthesize the SHINC-3 polypeptide of the present invention. General means for the production of peptides, analogs or derivatives are known in the art (see, e.g., Chemistry and Biochemistry of Amino Acids, Peptides, and Proteins—A Survey of Recent Developments, B. Weinstein, ed. (1983)). Substitution of D-amino acids for the normal L-stereoisomer can be carried out to increase the half-life of the molecule. Methods for preparation of the SHINC-3 protein or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, J. Am. Chem. Soc. 85:2149, 1963 which is incorporated by reference) or the FMOC strategy on a Rapid Automated Multiple Peptide Synthesis system (E. I. du Pont de Nemours Company, Wilmington, Del.) (Caprino and Han, J. Org. Chem. 37:3404, 1972 which is incorporated by reference).

As noted above, a SHINC-3 protein can be or comprise a epitope-bearing portion of the polypeptide encoded by a nucleic acid sequence comprising SEQ ID NO:2. Such SHINC-3 proteins can be used to create antibodies using standard immunological techniques. Polyclonal or monoclonal antibodies to the protein or an epitope thereof can be made for use in immunoassays by any of a number of methods known in the art. By epitope reference is made to an antigenic determinant of a polypeptide. An epitope could comprise 3 amino acids in a spatial conformation which is unique to the epitope. Generally an epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse.

Oligopeptides can be selected as candidates for the production of an antibody to the SHINC-3 protein based upon the oligopeptides lying in hydrophilic regions, which are thus likely to be exposed in the mature protein. Peptide sequence used to generate antibodies against any fragment of SHINC-3 that typically is at least 5-6 amino acids in length, optionally fused to an immunogenic carrier protein, e.g. KLH or BSA. Additional oligopeptides can be determined using, for example, the Antigenicity Index, Welling, G. W. et al., FEES Lett. 188:215-218 (1985), incorporated herein by reference.

In other embodiments of the present invention, humanized monoclonal antibodies are provided, wherein the antibodies are specific for SHINC-3. The phrase "humanized antibody" refers to an antibody derived from a non-human antibody, typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans.

The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., Nature 321:522-525 (1986); Morrison et al., Proc. Natl. Acad. Sci, USA, 81:6851-6855 (1984); Morrison and Oi, Adv. Immunol, 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 40:773-83 (1991) each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* 196:901-917 (1987); Kabat et al., U.S. Dept. of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g, via Ashwell receptors. See, e.g., U.S. Pat. Nos. 5,530,101 and 5,585,089 which patents are incorporated herein by reference.

Humanized antibodies to SHINC-3 can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy-and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art; and are used in immunization of, for example, a transgenic mouse as described in WO 96/33735. This publication discloses monoclonal antibodies against a variety of antigenic molecules including IL-6, IL-8, TNF, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils.

Human monoclonal antibodies with specificity for the antigen used to immunize transgenic animals are also disclosed in WO 96/34096.

In the present invention, SHINC-3 polypeptides of the invention and variants thereof are used to immunize a transgenic animal as described above. Monoclonal antibodies are made using methods known in the art, and the specificity of the antibodies is tested using isolated SHINC-3 polypeptides.

Polyclonal antibodies can be prepared by immunizing rabbits or other animals by injecting antigen followed by subsequent boosts at appropriate intervals. The animals are bled and sera assayed against purified SHINC-3 protein usually by ELISA or by bioassay based upon the ability to block the action of SHINC-3. In a non-limiting example, an antibody to SHINC-3 can block the binding of SHINC-3 to Disheveled protein. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler, *Nature* 256:495-497, 1975; Gulfre and Milstein, *Methods in Enzymology: Immunochemical Techniques* 73:1-46, Langone and Banatis eds., Academic Press, 1981 which are incorporated by reference). The hybridoma cells so formed are then cloned by limiting dilution methods and supernates assayed for antibody production by ELISA, RIA or bioassay.

Specific antibodies, either polyclonal or monoclonal, to the SHINC-3 protein can be produced by any suitable method known in the art as discussed above. For example, murine or human monoclonal antibodies can be produced by hybridoma technology or, alternatively, the SHINC-3 protein, or an immunologically active fragment thereof, or an anti-idiotypic antibody, or fragment thereof can be administered to an animal to elicit the production of antibodies capable of recognizing and binding to the SHINC-3 protein. Such antibodies can be from any class of antibodies including, but not limited to IgG, IgA, IgM, IgD, and IgE or in the case of aviari species, IgY and from any subclass of antibodies. For example, such a SHINC-3 protien can be used to inoculate a suitable host animal (a rabbit, a mouse, a rat, a goat, etc.) which will generate antibodies against the epitope. If needed, one or more booster inoculations can be performed. Ultimately, sera from the inoculate animals can be obtain, which cn contain an antibody that binds specifically to a SHINC-3 protein including the epitope (e.g., to a polypeptide having amino acids at least 95% identical to amino acids encoded by at least 300 contiguous nucleic acids from SEQ ID NO:2).

Antibodies can be purified from the sera of such host animals. Alternatively, a SHINC-3 antobody-producing animal can be used to create hybridomas secreting monoclonal antibodies using standard techniques. However produced, the invention includes an antibody that binds specifically to a SHINC-3 polypeptide, such as a polyclonal or a monoclonal antibody. Desirably, the antibody is isolated (i.e., separated from the host animal that produced it), but it can be in a serum or other medium that also contains other antibodies.

In another embodiment, the invention provides diagnostic or methods or methods of detection involving SHINC-3 polynucleotides or polypeptides. For example, in one embodiment, the invention provides a method of identifying compounds (e.g., small molecules, proteins, or other compounds) that modulate apoptosis. In accordance with the method, compounds are assayed to identify those binding to SHINC-3 polypeptide. Any suitable protocol can be used to identify compounds binding or interacting with the SHINC-3 polypeptide. For example, a SHINC-3 polypeptide can be exposed both to an anti-SHINC-3 antibody and the test compound to assess whether the test compound can compete with the antibody for binding to SHINC-3. Compounds that are able to interfere with antibody binding are candidate compounds for modulators of apoptosis. In another type of assay, SHINC-3 polypeptide can be immobilized on a support and probed with a preparation (e.g., a solution or suspension) of the test compound similar to an ELISA.

In a number of circumstances it would be desirable to determine the levels of SHINC-3 in a patient. The identification of SHINC-3 along with the present report showing expression of SHINC-3 provides the basis for the conclusion that the presence of SHINC-3 serves a normal physiological function related to cell growth and survival. Endogenously produced SHINC-3 may also play a role in certain disease conditions, such as cancer. Accordingly, the invention provides a method of detecting or evaluating the prognosis of a cancer characterized by a change in expression of SHINC-3. To detect the presence of SHINC-3 in a patient, a sample is obtained from the patient. In accordance with this method, an analyte is obtained from a patient or a biopsy tissue. The anaylte can be a tissue biopsy sample or a sample of blood, plasma, serum, CSF or the like. SHINC-3 tissue expression is disclosed in the examples. Samples for detecting SHINC-3 can be taken from these tissue. When assessing peripheral levels of SHINC-3, it is preferred that the sample be a sample of blood, plasma or serum. When assessing the levels of SHINC-3 in the central nervous system a preferred sample is a sample obtained from cerebrospinal fluid or neural tissue Thereafter, the analyte is probed for the expression of SHINC-3. The analyte can be assayed to detect the SHINC-3 protein or genetic expression. The term "detection" as used herein in the context of detecting the presence of SHINC-3 in a patient is intended to include the determining of the amount of SHINC-3 or the ability to express an amount of SHINC-3 in a patient, the estimation of prognosis in terms of probable outcome of a disease and prospect for recovery, the monitoring of the SHINC-3 levels over a period of time as a measure of status of the condition, and the monitoring of SHINC-3 levels for determining a preferred therapeutic regimen for the patient.

Any suitable method of detection can be used. Thus, for example, SHINC-3 genetic expression in the analyte can be assessed using PCT (e.g., rtPCR) techniques, or Northern or Southern blot hybridization. SHINC-3 protein levels in the analyte can be assessed, for example, using immunihistochemical techniques, ELISA being a preferred technique. However, assessed, the amount of SHINC-3 protein and/or genetic expression in the analyte is compared to the amount of SHINC-3 protein and/or genetic expression in normal tissue (e.g., control tissue). Abnormally high or low amount of SHINC-3 protein and/or genetic expression in the analyte in comparison to the analyte can be correlated to a cancerous condition. Accordingly, such a comparison can be used to detect cancer in a patient, particularly a cancer characterized by SHINC-3 overexpression or underexpression. The method also can be used to evaluate the prognosis of such a cancer.

The availability of SHINC-3 allows for the identification of small molecules and low molecular weight compounds that inhibit the binding of SHINC-3 to binding partners, through routine application of high-throughput screening methods (HTS). HTS methods generally refer to technologies that permit the rapid assaying of lead compounds for therapeutic potential. HTS techniques employ robotic handling of test materials, detection of positive signals, and interpretation of data. Lead compounds may be identified via the incorporation of radioactivity or through optical assays that rely on absorbence, fluorescence or luminescence as read-outs. Gonzalez, J. E. et al., (1998) *Curr. Opin. Biotech.* 9:624-631.

Model systems are available that can be adapted for use in high throughput screening for compounds that inhibit the interaction of SHINC-3 with its ligand, for example by competing with SHINC-3 for ligand binding. Sarubbi et al., (1996) *Anal. Biochem.* 237:70-75 describe cell-free, nonisotopic assays for discovering molecules that compete with natural ligands for binding to the active site of IL-1 receptor. Martens, C. et al., (1999) *Anal. Biochem.* 273:20-31 describe a generic particle-based nonradioactive method in which a labeled ligand binds to its receptor immobilized on a particle; label on the-particle decreases in the presence of a molecule that competes with the labeled ligand for receptor binding.

SHINC-3 may also be used in screens to identify drugs for treatment of cancers which involve over-activity-of the encoded protein, or new targets which would be useful in the identification of new drugs.

In some instances it is desirable to determine whether the SHINC-3 gene is intact in the patient or in a tissue or cell line within the patient. By an intact SHINC-3 gene, it is meant that there are no alterations in the gene such as point mutations, deletions, insertions, chromosomal breakage, chromosomal rearrangements and the like wherein such alteration might alter production of SHINC-3 or alter its biological activity, stability or the like to lead to disease processes. Thus, in one embodiment of the present invention a method is provided for detecting and characterizing any alterations in the SHINC-3 gene. The method comprises providing an oligonucleotide that contains the SHINC-3 cDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarity to the sequence from which it is derived to hybridize to the SHINC-3 gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact SHINC-3 gene or a SHINC-3 gene abnormality.

Hybridization to a SHINC-3 gene would involve denaturing the chromosomal DNA to obtain a single-stranded DNA; contacting the single-stranded DNA with a gene probe associated with the SHINC-3 gene sequence, and identifying the hybridized DNA-probe to detect chromosomal DNA containing at least a portion of a human SHINC-3 gene.

The term "probe" as used herein refers to a structure comprised of a polynucleotide that forms a hybrid structure with a target sequence, due to complementarity of probe sequence with a sequence in the target region. Oligomers suitable for use as probes may contain a minimum of about 8-12 contiguous nucleotides which are complementary to the targeted sequence and preferably a minimum of about 20.

The SHINC-3 gene probes of the present invention can be DNA or RNA oligonucleotides and can be made by any method known in the art such as, for example, excision, transcription or chemical synthesis. Probes may be labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification. Hybridization is typically carried out at 25°-45° C., more preferably at 32°-40° C. and more preferably at 37°-38° C. The time required for hybridization is from about 0.25 to about 96 hours, more preferably from about one to about 72 hours, and most preferably from about 4 to about 24 hours.

SHINC-3 gene abnormalities can also be detected by using the PCR method and primers that flank or lie within the SHINC-3 gene. The PCR method is well known in the art. Briefly, this method is performed using two oligonucleotide primers which are capable of hybridizing to the nucleic acid sequences flanking a target sequence that lies within a SHINC-3 gene and amplifying the target sequence. The terms "oligonucleotide primer" as used herein refers to a short strand of DNA or RNA ranging in length from about 8 to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, a method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising SHINC-3 or a fragment thereof is then directly sequenced and analyzed by comparison of the sequence with the sequences disclosed herein to identify alterations which might change activity or expression levels or the like.

In another embodiment, a method for detecting SHINC-3 is provided based upon an analysis of tissue expressing the SHINC-3 gene. Certain tissues such as those identified below have been found to express the SHINC-3 gene. The method comprises hybridizing a polynucleotide to mRNA from a sample of tissue that normally expresses the SHINC-3 gene. The sample is obtained from a patient suspected of having an abnormality in the SHINC-3 gene or in the SHINC-3 gene of particular cells.

To detect the presence of mRNA encoding SHINC-3 protein, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques. The mRNA of the sample is contacted with a DNA sequence serving as a probe to form hybrid duplexes. The use of a labeled probes as discussed above allows detection of the resulting duplex.

When using the cDNA encoding SHINC-3 protein or a derivative of the cDNA as a probe, high stringency conditions can be used in order to prevent false positives, that is the hybridization and apparent detection of SHINC-3 nucleotide sequences when in fact an intact and functioning SHINC-3 gene is not present. When using sequences derived from the SHINC-3 cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook et al., 1989, supra).

In order to increase the sensitivity of the detection in a sample of mRNA encoding the SHINC-3 protein, the technique of reverse transcription/polymerization chain reaction (RT/PCR) can be used to amplify cDNA transcribed from mRNA encoding the SHINC-3 protein. The method of RT/PCR is well known in the art, and can be performed as follows. Total cellular RNA is isolated by, for example, the standard guanidium isothiocyanate method and the total RNA is reverse transcribed.

The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and SHINC-3 specific primers. (Belyavsky et al, *Nucl. Acid Res.* 77:2919-2932, 1989; Krug and Berger, *Methods in Enzymology,* 152:316-325, Academic Press, NY, 1987 which are incorporated by reference).

The polymerase chain reaction method is performed as described above using two oligonucleotide primers that are substantially complementary to the two flanking regions of the DNA segment to be amplified. Following amplification, the PCR product is then electrophoresed and detected by ethidium bromide staining or by phosphoimaging.

The present invention further provides for methods to detect the presence of the SHINC-3 protein in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (*Basic and Clinical Immunology,* 217-262, Sites and Terr, eds., Appleton & Lange, Norwalk, Conn., 1991, which is incorporated by reference). Preferred are binder-ligand immunoassay methods including reacting antibodies with an epitope or epitopes of the SHINC-3 protein and competitively displacing a labeled SHINC-3 protein or derivative thereof.

As used herein, a derivative of the SHINC-3 protein is intended to include a polypeptide in which certain amino acids have been deleted or replaced or changed to modified or unusual amino acids wherein the SHINC-3 derivative is biologically equivalent to SHINC-3 and wherein the polypeptide derivative cross-reacts with antibodies raised against the SHINC-3 protein. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays; e.g., enzyme-linked immuriosorbent assay (ELISA), fluorescent immunoassays and the like.

In another aspect, the invention provides therapeutic methods. For example, the invention provides a method of treating or preventing a cancer characterized by variation in the expression of SHINC-3 comprising administering a compound that inhibits or promotes SHINC-3 gene expression and/or activity of the SHINC-3 polypeptide. For example, the cell to be treated in accordance with the inventive method can be selected from the group of cancer cells consisting of lung cancer, bronchus cancer, colorectal cancer, prostate cancer, breast cancer, pancreas cancer, stomach cancer, ovarian cancer, urinary bladder cancer, brain or central nervous system cancer, peripheral nervous system cancer, esophageal cancer, cervical cancer, melanoma, uterine or endometrial cancer, cancer of the oral cavity or pharynx, liver cancer, kidney cancer, biliary tract cancer, small bowel or appendix cancer, salivary gland cancer, thyroid cancer, adrenal gland cancer, osteosarcoma, chondrosarcoma, liposarcoma, and testes cancer. Of course, other types of cancer cells also can be treated in accordance with the inventive method. Preferred cancers for treatment in accordance with the inventive method include breast cancer, leukemia, lymphoma, melanoma, colorectal cancer, and lung cancer.

In one embodiment, the invention provides a method of modulating apoptosis, proliferation, or protein trafficking of a cancer cell, comprising regulating expression of SHINC-3 in the cancer cell. Regulation of expression of SHINC-3 can be achieved by delivering to the cell an agent that interferes with the expression of SHINC-3. One such agent is an antisense SHINC-3 polynucleotide, which can be delivered to the cell as naked DNA or within a genetic vector as herein described. Alternatively, the regulation of expression of SHINC-3 can be regulated by introducing into the cell a ribozyme or an interfering RNA (siRNA, or RNAi) (which also are agents that interfere with the expression of SHINC-3) 3, as herein described. Thus, the inventive method can be used to treat a cancer characterized by SHINC-3 overexpression, comprising administering an agent that inhibits SHINC-3 expression. Similarly, the inventive can be employed to inhibit cancer cell proliferation and/or metastasis in a cancer patient comprising administering an agent that inhibits SHINC-3 expression to the patient.

The unique ability of antibodies to recognize and specifically bind to target proteins provides an approach for treating an overexpression of the protein. Thus, another aspect of the present invention provides for a method for preventing or treating diseases involving overexpression of the SHINC-3 protein by treatment of a patient with specific antibodies to the SHINC-3 protein. For example, a cancer characterized by SHINC-3 overexpression can be treated by administering an antibody that specifically binds SHINC-3 to the cancer cell. The antibody binds the SHINC-3 protein and inhibits its activity. Thus, the method can be employed to inhibit cancer cell proliferation and/or metastasis through the use of SHINC-3 antibodies.

Where the method is employed to attenuate the progression of cancer within a patient, or to attenuate the growth of a tumor, cell proliferation or metastasis in a patient, the method need not achieve complete elimination or remission of the cancer or tumor. In this regard, a successful therapeutic treatment can include halting the progression of the cancer or tumor, thereby enlarging the time that the growing cancer or tumor can be treated by other methods. In this regard, the inventive method can be employed adjunctively with other methods and reagents for treating cancerous cells and tumor. For example; the method can be employed in conjunction with radiation therapy of cancers or tumors. Alternatively, the inventive method can be used in conjunction with chemotherapeutic methods or hormone or biological therapy. Thus, when used to treat cancer cells, the inventive method can include adjunctively exposing the cell or cells to be treated, or a tumor containing them, with one or more antineoplastic agents or other drugs, many of which are known in the art. For example, drugs or active agents for adjunctive use in conjunction with the inventive method can include anticancer agents (e.g., chemotherapeutic agents), in that they are capable of inducing (either directly or indirectly) cancer cell or tumor cell cytotoxicity. Exemplary anticancer agents include mitoxantrone, taxanes, paclitaxel, camptothecin, camptothecin derivaties (e.g., SN-38), topotecan, gemcitabine, vinorelbine, vinblastine, anthracyclines, adriamycin, capecitabine, doctaxel, didanosine (ddl), stavudine (d4T), antisense oligonucleotides (e.g., c-raf antisense oligonucleotide (RafAON)), antibodies (e.g., herceptin), immunotoxins, hydroxyurea, melphalan, chlormethine, extramustinephosphate, uramustine, ifosfamide, mannomustine, trifosfamide, streptozotocin, mitobronitol, mitoxantrone, methotrexate, 5-fluorouracil, cytarabine, tegafur, idoxide, taxol, daunomycin, daunorubicin, bleomycin, amphotericin, carboplatin, cisplatin, BCNU, vincristine, camptothecin, mitomycin, doxorubicin, etopside, histernine dihydrochloride, tamoxifen, cytoxan, leucovorin, oxaliplatin, irinotecan, raltitrexed, epirubicin, anastrozole, proleukin, sulindac, EKI-569, erthroxylaceae, cerubidine, docetaxel, cytokines (e.g., interleukins), ribozymes, interferons, oligonucleotides, and functional derivatives of the foregoing.

In another embodiment, the invention provides a method of treating a condition characterized by SHINC-3 underexpression. In accordance with the method, an agent that promotes SHINC-3 expression is delivered to a cell so as to promote expression of SHINC-3 within the cell. The cell can be isolated or within a desired tissue type, as desired, such as within a patient. Any suitable agent can be used to promote expression of SHINC-3, such as an expression cassette encoding SHINC-3. Such a cassette can be within a vector, as herein described, if desired.

The present invention also includes therapeutic or pharmaceutical compositions comprising SHINC-3 in an effective amount for treating patients with disease, and a method comprising administering a therapeutically effective amount of SHINC-3. These compositions and methods are useful for treating a number of diseases including cancer. One skilled in the art can readily use a variety of assays known in the art to determine whether SHINC-3 would be useful in promoting survival or functioning in a particular cell type.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation.

SHINC-3 polypeptides, antibodies, or polynucleotides can also be linked or conjugated with agents that provide desirable pharmaceutical or pharmacodynamic properties. For example, SHINC-3 can be coupled to any substance known in the art to promote penetration or transport across the blood-brain barrier such as an antibody to the transferrin receptor, and administered by intravenous injection (see, for example, Friden et al., *Science* 259:373-377, 1993 which is incorporated by reference). Furthermore, SHINC-3 can be stably linked to a polymer such as polyethylene glycol to obtain desirable properties of solubility, stability, half-life and other pharmaceutically advantageous properties. (See, for example, Davis et al., *Enzyme Eng.* 4:169-73, 1978; Buruham, *Am. J. Hosp. Pharm.* 51:210-218, 1994 which are incorporated by reference.).

In another example, the invention provides a diagnostic composition including an oligonucleootide that specifically binds at least five nucleotides of the SHINC-3 DNA or an antibody that specifically binds a SHINC-3 protein, either of which is attached directly or indirectly to a label. The label can be a substrate for an enzyme (e.g., b-galactosidase, horseradish peroxidase, etc.) a chemiluminescent moiety, a radioactive isotope, or other label. Typically, such a diagnostic composition also will include a diagnostically acceptably carrier. The diagnostic composition can be used to detect cancer via probing for the expression of SHINC-3, as described herein.

In another embodiment, the invention provides a formulation of an antisense oligonucleootide specific to SHINC-3, such as described herein. Desirably, the composition also includes cytotoxic moieties, such as chemotherapeutic agents, ad/or radionucleotides. Of course, for therapeutic application, such a composition also can include a pharmaceutically-acceptable carrier. Such a formulation can be used to modulate tumor growth and metastasis, as described herein.

In another embodiment, the invention provides a composition including an agonist or antagonist of SHINC-3 expression and/or activity and a pharmaceutically-acceptable carrier. Exemplary agonists of SHINC-3 expression and/or activity include SHINC-3 expression cassettes or constructs, as well as vectors containing them, for example; as discussed herein. Exemplary antagonists of SHINC-3 expression and/or activity include antisense SHINC-3 polynucleotides or SHINC-3-binding antiboies, as described herein. Such compositions can be used for the treatment of cancer, for example, as described above.

The compositions of the present invention are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. SHINC-3 antibodies, polynucleotides or polypeptides can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion. Dose administration can be repeated depending upon the pharmacokinetic parameters of the dosage formulation and the route of administration used.

It is also contemplated that certain formulations containing SHINC-3 antibodies, polynucleotides or polypeptides are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, SHINC-3 antibodies, polynucleotides or polypeptides may be therapeutically administered by implanting into patients vectors or cells capable of producing a biologically-active form of SHINC-3 antibodies, polynucleotides or polypeptides or a precursor of SHINC-3, i.e., a molecule that can be readily converted to a biological-active form of SHINC-3 by the body. In one approach cells that secrete SHINC-3 may be encapsulated into semipermeable membranes for implantation into a patient. The cells can be cells that normally express SHINC-3 or a precursor thereof or the cells can be transformed to express SHINC-3 or a precursor thereof. It is preferred that the cell be of human origin and that the SHINC-3 be human SHINC-3.when the patient is human. However, the formulations and methods herein can be used for veterinary as well as human applications and the term "patient" as used herein is intended to include human and veterinary patients.

The therapeutic SHINC-3 polynucleotides (including antisense polynucleotides) and polypeptides of the present invention may be utilized in gene delivery vehicles. The gene delivery vehicle may be of viral or non-viral origin (see generally, Jolly, *Cancer Gene Therapy* 1:51-64 (1994); Kimura, *Human Gene Therapy* 5:845-852 (1994); Connell, *Human Gene Therapy* 1:185-193 (1995); and Kaplitt, *Nature Genetics* 6:148-153 (1994). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/07936; WO 94/03622; WO 93/25698; WO 93/25234; U.S. Pat. No. 5,219,740; WO 93/11230; WO 93/10218; Vile and Hart, *Cancer Res.* 53:3860-3864 (1993); Vile and Hart, *Cancer Res.* 53:962-967 (1993); Ram et al., *Cancer Res.* 53:83-88 (1993); Takamiya et al., *J. Neurosci. Res.* 33:493-503 (1992); Baba et al., *J. Neurosurg.* 79:729-735 (1993); U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., */. Vir.* (63:3822-3828 (1989); Mendelson et al., *Virol* 166:154-165 (1988); and Flotte et al., *P.N.A.S.* 90:10613-10617 (1993).

Representative examples of adenoviral vectors include those described by Berkner, *Biotechniques* 6:616-627 (Biotechniques); Rosenfeld et al., *Science* 252:431-434 (1991); WO 93/19191; Kolls et al., *P.N.A.S.* 215-219 (1994); Kass-Bisleret al., *P.N.A.S.* 90:11498-11502 (1993); Guzman et al., *Circulation* 55:2838-2848 (1993); Guzman et al., *Cir. Res.* 73:1202-1207 (1993); Zabner et al., *Cell* 75:207-216 (1993); Li et al., *Hum. Gene Ther.* 4:403-409 (1993); Cailaud et al., *Eur. J. Neurosci.* 5:1287-1291 (1993); Vincent et al., *Nat. Genet.* 5:130-134 (1993); Jaffe et al., *Nat. Genet.* 7:372-378 (1992); and Levrero et al., *Gene* 101:195-202 (1992). Exemplary adenoviral gene therapy vectors employable in this invention also include those described-in WO 94/12649, WO 93/03769; WO 93/19191; WO 94/28938; WO 95/11984 and WO 95/00655. Administration of DNA linked to killed adenovirus as described in Curiel, *Hum. Gene Ther.* 3:147-154 (1992) may be employed.

Other gene delivery vehicles and methods may be employed, including polycationic condensed DNA linked or unlinked to killed adenovirus alone, for example Curiel, *Hum. Gene Ther.* 3:147-154 (1992); ligand-linked DNA, for example see Wu, *J. Biol. Chem.* 264:16985-16987 (1989); eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Biol.* 14:2411-2418 (1994), and in Woffendin, *Proc. Natl. Acad. Sci.* 91:1581-1585 (1994).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene-delivery vehicles are described in U.S. Pat. No. 5,422,120, PCT Patent Publication Nos. WO 95/13796, WO 94/23697, and WO 91/14445, and EP No. 0 524 968.

Further non-viral delivery suitable for use includes mechanical delivery systems such as the approach described in Woffendin et al, *Proc. Natl. Acad. Sci. USA* P7(24):11581-11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033.

A preferred composition including SHINC-3 antibodies, polynucleotides or polypeptides is a liposomal formulation. Liposomal preparations of oligonucleotides and proteins are known in the art, and any suitable method can be employed to manufacture a liposomal formulation of SHINC-3 antibodies, polynucleotides or polypeptides. Where the formulation includes a SHINC-3 polynucleotide (e.g., a SHINC-3 antisense polynucleotide), a preferred formulation can be as described in U.S. Pat. No. 6,333,314; see also Felgner, Editorial, Human Gene Therapy 7:1791-1793, 1996).

For all of the preceding embodiments, the clinician will determine, based on the specific condition, whether SHINC-3 polypeptides or polynucleotides, antibodies to SHINC-3, or small molecules such as peptide analogues or antagonists, will be the most suitable form of treatment. These forms are all within the scope of the invention.

EXAMPLE 1

Materials and Methods

Cell culture—DU-145 human prostate cancer cells and MDA-MB231 human breast cancer cells were grown in improved minimum essential medium (Cellgro) containing 10% fetal bovine serum and 2 mM L-glutamine in a humidified atmosphere of 5% CO2: 95% air at 37° C. Logarithmically growing DU-145 cells were treated with a 20-mer phosphorothioate antisense oligodeoxyribonucleotide of raf-1 (ASR) (ISIS 13650) to block raf-1 expression and mismatched phosphorothioate antisense oligodeoxyribonucleotide of raf-1 (MM) (ISIS 10353) were used to show antisense raf-1 sequence specificity. Briefly, DU-145 cells treated with various concentration of either ASR or MM were incubated for 6 hr in the presence of lipofectin (15 μg/ml) (Life technologies, Gaithersburg, Md.) in Improved Minimum Essential Medium (IMEM) containing 1% fetal bovine serum (FBS). Cells were then washed twice with 10% FBS-containing medium to remove any residual lipofectin and maintained overnight in 1% FBS-containing medium in the presence of either ASR or MM at concentrations indicated. On day 2, cells were treated with the same cycle as specified for day 1 and continued for an additional 24 hr. On day 3, cells were subjected to either Northern blot or Western blot analyses. For Northern blot analysis, cells were treated as described above with either ASR (0.5 μM) or MM (0.5 μM).

cDNA Synthesis and Differential Display of mRNAs (DD-RTPCR)—Total cellular RNA was extracted using RNAzol B (Tel-Test Inc. Texas). The RNA was further cleaned off chromosomal contamination by treating with DNase 1 using the MessageClean kit according to the manufacturer's instructions (GenHunter, Brookline, Mass.), In the presence of anchor primer (HT11-A, HT11-C, HT11-G; GenHunter) and 100 U of MMLV Reverse Transcriptase (GenHunter) 0.2 μg of RNA was used in reverse transcription reaction (Rt) according to the manufacturer's instructions (GenHunter). cDNA was then either stored at −20° C. or used in a polymerase chain reaction (PCR). PCR was carried out according to the RNAimage kit (GenHunter). Briefly 2 μl of Rt mix was used in a reaction with 0.2 μM of the same anchor primer as used in the cDNA generation and 0.2 μM of an arbitrary primer (H-AP1-H-AP8; GenHunter), 2 μM dNTP, 10 μCi $^{33}$P-dATP (1250 Ci/mmol; NEN Dupont, Boston, Mass.) and 1 unit of Amplitaq (Perkin Elmer, Branchburg, N.J.). The reactions were subjected to 40 cycles at 94° C. for 30 sec, 40° C. for 2 min, and 72° C. for 30 sec, followed by a final soak temperature of 72° C. for 5 min on the 9600 Perkin Elmer thermal cycler (Perkin Elmer). The reactions were then stored −20° C. To examine the differentially displayed mRNAs, 3.5 (μl of sample was mixed with 2 μl of loading dye (GenHunter), incubated at 80° C. for 5 min, and electrophoresed on a 6% denaturing polyacrylamide gel, followed by autoradiography.

Reamplification and Cloning of cDNA Fragments—Bands of interest were located on the differential display gel and cut out, and DNA was eluted by soaking the bands in 100 μl of H$_2$O for 10 min and then boiling for 15 min. The supernatant was ethanol-precipitated and then sample was dissolved in 10 μl of H$_2$O and reamplified using the original combination of the arbitrary and anchor primers according to the instructions in the RNAimage kit. If the amplified product was not detectable by 1.5% agarose gel electrophoresis, a third-step PCR as described above was carried out using a 1:10 dilution of the reamplified PCR product. The PCR product was cloned into the PCR 2.1 cloning vector according to the TA cloning kit instructions (Invitrogen, San Diego, Calif.). Plasmid DNA isolation from overnight cultures of the transformed *E. coli* cells (One Shot, INV_F'; Invitrogen) was carried out by the alkaline lysis and phenol/chloroform extraction method (Maniatis et al., 1982). Size of the insert cDNA was determined by restriction digestion with EcoRl, followed by agarose gel electrophoresis. Inserts of expected sizes were purified from the agarose gel according to the Qiax 2 kit (Qiagen, Chatsworth, Calif.).

cDNA Sequencing—The partial cDNA clones representing differentially expressed mRNAs were sequenced in both directions, using either the T7 or M13 reverse primer (Perkin Elmer) by the automated DNA sequencer (Applied Biosystems, Perkin Elmer). The cDNA sequences were subsequently entered in the DNA database (DDBJ, GenBank and GenEMBL) to examine the homology to the known genes. Northern Blot Hybridization Analysis—Total RNA extracted from DU-145 cells or MDA-MB231 cells was fractionated on a 1.0% formaldehyde agarose gel and transferred onto nylon membrane (Qiagen) and fixed by UV cross-linking. cDNA inserts and human GAPDH cDNA probe were radiolabeled with $^{32}$P-dCTP using a random primer DNA labeling kit (Pharmacia Biotech, Piscataway, N.J.). Blots were sequentially hybridized first to a radiolabeled partial human cDNA probe and then to human GAPDH cDNA probe at 68° C. in ExpressHyb hybridization solution (Clontech, Palo Alto, Calif.). Blots were washed three times in 2×SSC and 0.05% SDS at 68° C., 2 times in 0.1×SSC and 0.1% SDS at 50° C. Dried blots were exposed to X-ray films. Autoradiographs were computer-scanned using the Image-Quant software, version 5.1 (Molecular Dynamics, Sunnyvale, Calif.). Expression of SHINC-2 and SHINC-3 cDNA fragment were also examined on 2 μg per lane poly (A)$^+$ mRNA blots of multiple human tissue and human cancer cell lines (Clontech). These blots were sequentially hybridized with human (β-actin cDNA probe according to the manufacturer's instructions.

a. Western Blotting

For Western blotting, cells were lysed in lysis buffer (Clontech, Palo Alto, Calif.) and protein concentrations were determined by Bradford's methods. Whole cell lysates normalized for protein content were loaded and separated on 10% SDS-PAGE followed by immunoblotting with monoclonal anti-raf-1 antibodies (Transduction lab, Lexington, Ky.) and raf-1 expression was detected by ECL reagents (Amersham Corporation, Arlington Heights, Ill.). The same blot was stripped and reprobed with polyclonal anti-G3PDH antibodies (Trevigen, Gaithersburg, Md.).

b. Inhibition of Raf-1 Expression by ASR

Figure 1:
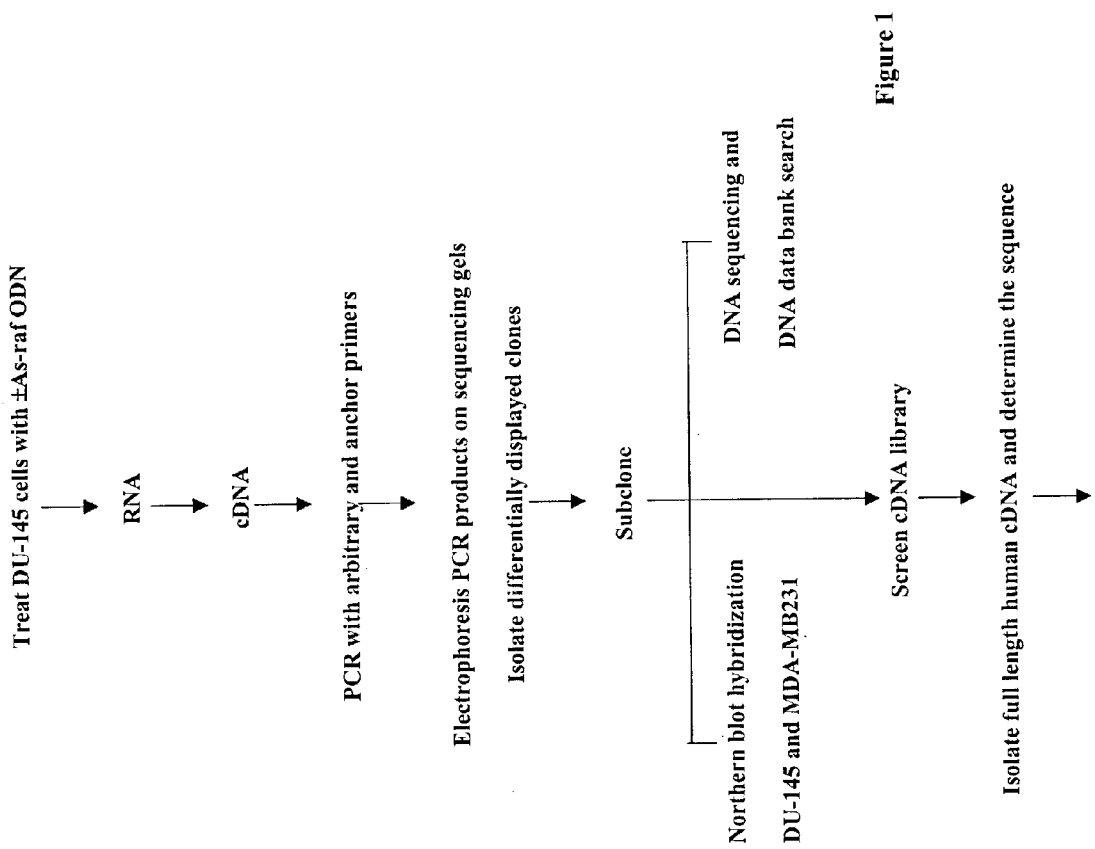
FIG. 1. Flow chart diagram of the differential display of mRNA approach used in this study.
Figure 2:
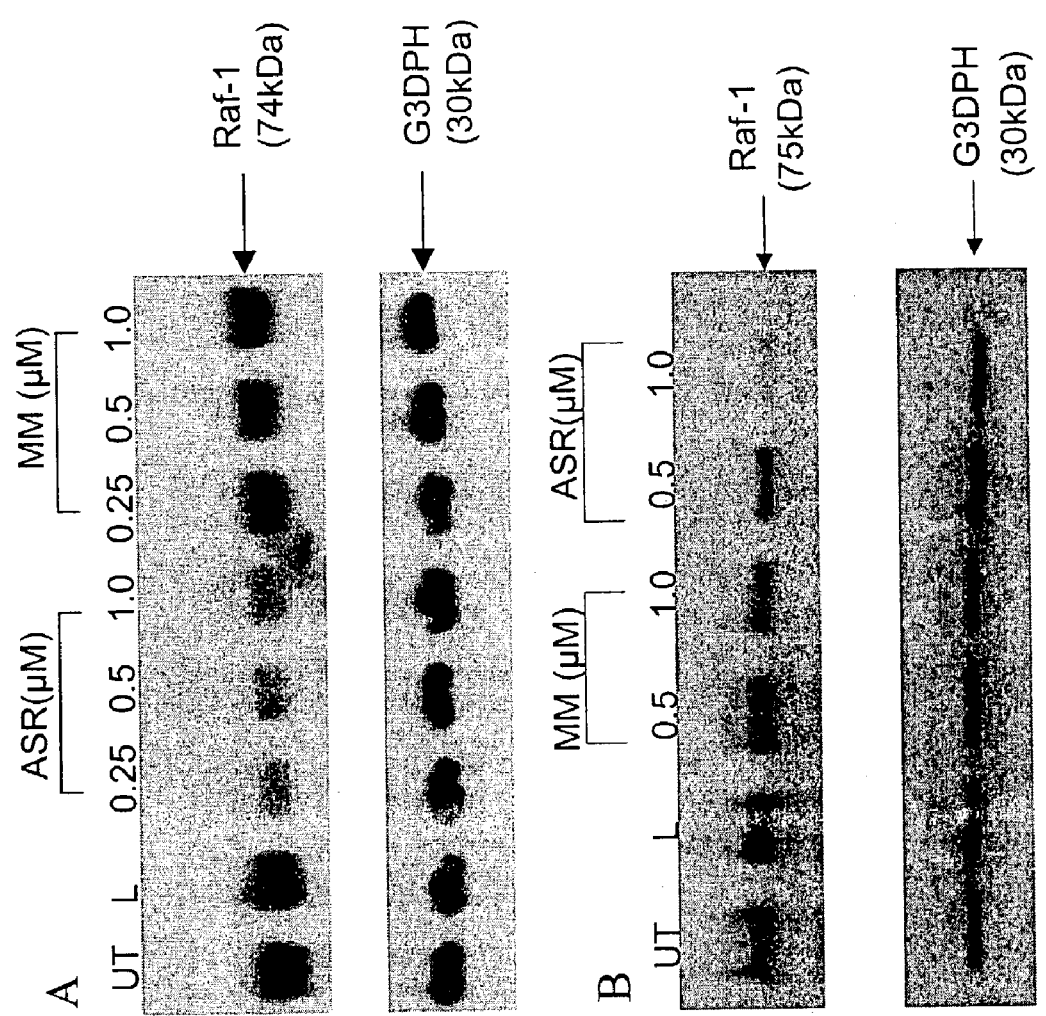
FIG. 2. Inhibition of Raf-1 protein expression by antisense raf oligonucleotide (ASR). Logarithmically growing Dul45 cells (A) and MDA-MB231(B) cells were treated with indicated concentration of either antisense raf oligonucleotide (ASR) or control mismatched antisense raf oligonucleotide (MM) as described in Materials and Methods. Control cells were either left untreated (UT), or treated lipofectin (15 ug/ml) (L). Whole cell lysates normalized for total protein content (25 µg/lane) were resolved on 10% SDS-PAGE followed by immunoblotting with monoclonal anti-Raf-1 antibody (1:4000 dilution). The same blot was stripped and reprobed with anti-G3DPH antibody (1:10,000 dilution).

We confirmed the inhibition of raf-1 expression by ASR in DU-145 cells and MDA-MB231 cells, ASR % inhibition ~80% for each concentration, and MM % inhibition ~20% according to densitometry (FIG. 2). ASR 0.5 μM and MM 0.5 μM were used for the treatment.

c. Selection of Differentially Displayed mRNAs in DU-145 Cells Treated with As-raf ODN We compared the patterns of differentially displayed mRNAs simultaneously in DU-145 cells treated with ASR, UT, L and MM. Ten different anchor and arbitrary primer combinations were tested to identify differentially displayed mRNAs in these four categories. The overall patterns of the amplified cDNA species were essentially the same and any specific differences within the cells were easily visually identifiable. Each primer combination displayed approximately 150-200 bands, each band theoretically representing one transcribed gene (Liang et al. 1992). The selection of a differentially expressed band was based on the presence of this band in ASR treated cells and its absence in UT-, L- and MM treated cells or the converse, i.e., the presence band in three control categories and its absence in ASR-treated cells. If a band was present in all of categories, selection was based on a significant visual difference in the band intensity noted in these two transfectant cell lines, hi the present study, 3 of 10 primer combinations used led to the identification of differentially expressed mRNAs: ASR-12a, ASR-12b, ASR-13, ASR-17, ASR-21, ASR-23 and ASR-25 (FIG. 3, Tables 1, 2) ASR-12b fragments was selected on the basis of the relatively higher band intensity in DU-145 cells treated with ASR whereas the other fragments were selected because of the relatively lower signal in DU-145 cells treated with ASR. The selected fragments were eluted from the gels, purified, and reamplified. Each fragment exhibited single band upon reamplification. The cDNA fragments were then cloned into the TA cloning vector.

d. Identification of Differentially Displayed mRNAs

Nucleotide sequencing analysis and DNA databank homology search of the partial cDNA fragments were performed and the data are shown in Table 2. ASR-12a was found to have % sequence homology in 225 bp overlap to human aspartyl β-hydroxylase (BAH), ASR-12b had 95% homology in 229 bp overlap to human specific structure recognition protein-1 (SSRP-1), ASR-13 had 100% homology in 247 bp overlap to human mitochondrial oxodicarboxylate carrier (OXDC), ASR-17 had % homology in 479 bp overlap to human ADP/ATP translocase (ANT) and ASR-23 had 100% homology in 193 bp overlap to human fatty aldehyde dehydrogenase (ALDH10/FALDH). The partial cDNA sequences of two other ftagments, ASR-21 (347 bp partial sequence and 2626 bp complete sequence) and ASR-25, which comprises, consists of, or consists essentially of the 191 bp partial sequence shown in FIG. 4 (SEQ ID NO: 1) and the 2684 complete sequence shown in FIG. 7 (SEQ ID NO:2), showed no significant homology to any of the sequences in the DDBJ, GenBank, GenEMBL or Human EST database, indicating that these two cDNAs may represent the novel genes (Table 2, FIG. 4).

e. Differential Expression of BAH. SSRP-1. OXDC. ANT and ALDH10 following the Treatment with ASR When Northern blots of DU-145 cells and MDA-MB231 cells were hybridized with the radiolabeled partial cDNA inserts (ASR-12a to ASR-23, Table 2), the expected sizes of the corresponding known transcripts and some bands with unknown size were observed (FIG. 5A). There was an approximately 200% overexpression of SSRP-1 in ASR-treated MDA-MB231 cells compared with that of MM-treated MDA-MB231 cells, but there was no significant change in that of DU-145 cells. An approximately 14% expression (86% inhibition) of 2.8 kb BAH band, 83% expression (17% inhibition) of 4.5 kb BAH band and 20% expression (80% inhibition) of 5.2 kb BAH band in ASR-treated DU-145 cells, compared with that of UT-DU-145 cells. An approximately 70% expression (30% inhibition) of 3.0 kb OXDC band, 50% expression (50% inhibition) of 4.5 kb OXDC band in ASR-treated DU-145 cells, compared with that of UT-DU-145 cells, but no significant change in 2.0 kb band. An approximately 42% expression (58% inhibition) of 4.0 kb ANT band in ASR-treated DU-145 cells, compared with that of MM-treated DU-145 cells, but no significant change in 1.3 kb band. An approximately 37% expression (63% inhibition) of 4.0 kb ALDH10 band in ASR-treated DU-145 cells, compared with that of UT-DU-145 cells (Table 3).

f. Differential Expression of Novel Genes following the Treatment with ASR in Human Normal Tissues and Cancer Cell Lines The partial cDNA fragments SHINC-2 and SHINC-3 (FIG. 4) were radiolabeled and hybridized to total RNA extracted from DU-145 cells. The SHINC-2 (~2.5 kb, ~3.5 kb and ~6.5 kb) and SHINC-3 (~2.5 kb, ~4.0 kb and ~8.5 kb) transcripts were seen in both UT-DU-145 cells and ASR-treated DU-145 cells. SHINC-2 expression was lower (~2.5 kb: 80%, ~3.5 kb: 24%, ~6.5 kb: 27%) in ASR-treated DU-145 cells than that of in UT-DU-145 cells. SHINC-3 expression was also lower (~2.5 kb: 42%, ~4.0 kb: 71%, ~8.5 kb: 50%) in ASR-treated DU-145 cells than that of UT-DU-145 cells (Table 2, FIG. 5B).

We found the 4.0 kb-transcript of BAH in DU-145 cells by Northern blot analysis, which matched to the known size (FIG. 5A). Analysis of the expression of SHINC-2 and SHINC-3 genes in normal human tissues indicated that, in general, SHINC-2 was relatively higher in heart, placenta, liver, skeletal muscle, spleen, prostate, testis and ovary, compared with that in brain, lung, kidney, pancreas, thymus, small intestine, colon and PBL, whereas SHINC-3 gene was present in prostate and testis (FIG. 5C). SHINC-2 was expressed in all cancer cell types examined, and SHINC-3 gene was highly expressed in two of eight cancer cell lines examined: lymphoblastic leukemia (MOLT-4), Burkitt's Ivmphoma (BL-Raji) (FIG. 5C).

In this application, we identified six (seven) novel components of the Raf-1-mediated signaling pathway. While the precise mechanism of induction of the specific gene expression remains to be studied, processing, and/or stability of several mRNAs, resulting in the differential expression of multiple factors. Identification of these distinct effectors also implies that Raf-1 may function via multiple pathways, which could be selectively utilized in different cell types.

EXAMPLE 2

This example demonstrates the development of an antibody specific for SHINC-3.

Rabbit SHINC-3 antisera were developed against a SHINC-3-specific peptide (KKVLDARGSNSLPLLR, 127-143 aa (SEQ ID NO:4)). The pMyc-SHINC-3 expression vector (FIG. 8) was transfected into Cos-1 cells. Cell lysate (1 mg of protein) then was immunoprecipitated with agarose-conjugated anti-myc antibody (Santa Cruz) and the immunoprecipitates were analyzed by immunoblotting with anti-SHINC-3 antiserum. Myc-tagged SHINC-3 protein was detected as about 28 kDa protein (See FIG. 11).

The present invention has been described with reference to specific embodiments. However, this invention is intended to cover those changes and substitutions, which may be made by those skilled in the art without departing from the spirit and scope of the appended claims.

All references, including publications, patent applications, and patents, cited herein, including those cited above and in the following list, are hereby incorporated by reference to the same extent as if each reference were individually and specifically indicated to be incorporated by reference and were set forth in its entirety herein.

REFERENCES

BRUDER, J. T., HEIDECKER, G., and RAPP, U. R. (1992). Serum-, TPA-, and Ras-induced expression from AP-1/Ets-driven promoters requires Raf-1 kinase. Genes Dev. 6, 545-556.

BRUHN, S. L., PIL, P. M., ESSIGMANN, J. M., HOUSMAN, D. E., and LIPPARD, S. J. (1992). Isolation and characterization of human cDNA clones encoding a high mobility group box protein that recognizes structural distions to DNA caused by binding of the anticancer agent cisplatin. Proc. Natl. Acad. Sci. USA 89, 2307-2311.

COZENS, A. L., RUNSWICK, M. J., and WALKER, J. E. (1989). DNA sequences of two expressed nuclear genes for human mitochondrial ADP/ATP translocase. J. Mol. Biol. 206, 261-280.

DAVIS, C. G. (1990). The many faces of epidermal growth factor repeats. New Biol. 2, 410-419.

DENT, P., HASER, W., HAYSTEAD, T. A. G., VINCENT, L. A., ROBERTS, T. M., STURGILL, T. W. (1992) Activation of mitogen-activated protein kinase kinase by v-Raf in NIH3T3 cells and in vitro. Science 257, 1404-1407.

DEVARY, Y., GOTTLIEB, R. A., SMEAL, T., and KARIN, M. (1992). The mammalian ultraviolet response is triggered by activation of Src tyrosine kinases. Cell 71, 1081-1091.

DINCHUK, J. E., HENDERSON, N. L., BURN, T. C., HUBER; R., HO, S. P., LINK, J., O'NEIL, K. T., FOCH, R. J., SCULLY, M. S., HOLLIS, J. M., HOLLIS, G. F., and FRIEDMAN, P. A. (2000). Aspartyl β-hydroxylase (Asph) and an evolutionarily conserved isoform of asph missing the catalytic domain share exons with junctin. J. Biol. Chem. 275, 39543-39554.

DOWNING, A. K., KNOTT, V., WERNER, J. M., CARDY, C. M., CAMPBELL, I. D., and HANDFORD, P. A. (1996). Solution structure of a pair of calcium-binding epidermal growth factor-like domains: implications for the Marfan syndrome and other genetic disorders. Cell 85, 597-605.

FIERMONTE, G., DOLCE, V., PALMIERI, L., VENTURA, M., RUNSWICK, M. J., PALMIER, F., and WALKER, J. E. (2001). Identification of the human mitochondrial oxodicarboxylate carrier. J. Biol. Chem. 276, 8225-8230.

FINCO, T., and BALDWIN, A. (1993). κB site-dependent induction of gene expression by diverse inducers of nuclear factor κB requires Raf-1. J. Biol. Chem. 268, 17676-17679.

GOKHALE, P. C., SOLDATENKOV, V., WANG, F-H, RAHMAN, A., DRITSCHILO, A., and KASID, U. (1997). Antisense raf oligodeoxyribonucleotide is protected by liposomal encapsulation and inhibits Raf-1 protein expression in vitro and in vivo: Implication for gene therapy of radioresistant cancer. Gene Therapy 4, 1289-1299.

GOKHALE, P. C., MCRAE, D., MONIA, B. P., BAGG, A., RAHMAN, A., DRITSHILO, A., and KASID, U. (1999). Antisense raf oligodeoxyribonucleotide is a radiosensitizer in vivo. Antisense Nucleio Acid Drug Dev. 9, 191-201.

GREEN, D. R., and REED, J. C. (1998). Mitochondria and Apoptosis. Science 281, 1309-1312.

GORUPPI, S., YAMANE, H., MARCANDALLI, P., GARCIA, A., CLOGSTON, C., GOSTISSA, M., VARNUM, B., and SCHNEIDER, C. (1997). The product of a gas6 splice variant allows the release of the domain responsible for Ax1 tyrosine kinase receptor activation. FEBS Lett. 415, 59-63.

HEIDECKER, G., HULEIHEL, M., CLEVELAND, J. L. KOLCH, W., BECK, T. W., LLOYD, P. PAWSON, T. and RAPP, U. R. (1990). Mutational activation of c-raf-1 and definition of the minimal transforming sequence. Mol. Cell. Biol. 10, 2503-2512.

HEIDECKER, G., KOLCH, W., MORRISON, D., and RAPP, U. R. (1992). The role of Raf-1 phosphorylation in signal transduction. Adv. Cancer Res. 58, 53-73.

HOULDWORTH, J. and ATTARDI, G. (1988). Two distinct genes for ADP/ATP translocase are expressed at the mRNA level in adult human liver. Proc. Natl. Acad. Sci. U.S.A. 85, 377-381.

HOWE, L. R., LEEVERS, S. J., GOMEZ, N., NAKIELNY, S., COHEN, P., and MARSHALL, C. L. (1992). Activation of the MAP kinase pathway by the protein kinase Raf. Cell 71, 335-342.

KASID, U., PFEIFER, A., WEICHSELBAUM, R. R., DRITSCHILO, A. and MARK, G. E. (1987). The raf oncogene is associated with a radiation-resistant human laryngeal cancer. Science 237, 1039-1041.

KASID, U., PFEIFER, A., BRENNAN, T., BECKETT, M., WEICHSELBAUM, R. R., DRITSCHILB, A., and MARK, G. E. (1989). Effect of antisense c-raf-1 on tumorigenicity and radiation sensitivity of a human squamous carcinoma. Science 243, 1354-1356.

KASID, U., PIROLLO, K., DRITSCHILO, A., and CHANG, E. (1993). Oncogenic basis of radiation resistance. Avd. Cancer Res. 61, 195-233.

KASID, U., SUY, S., DENT, P., RAY, S., WHITESIDE, T. L., and STURGILL, T. W. (1996). Activation of Raf by ionizing radiation. Nature 382, 813-816.

KELSON, T. L., SECOR MCVOY, J. R., and RIZZO, W. B. (1997). Human liver fatty aldehyde dehydrogenase: Microsomal localization, purification, and biochemical characterization. Biochim. Biophys. Acta. 1335, 99-110.

KOLAROV, J., KOLAROVA, N., and NELSON, N. (1990). A third ADP/ATP translocator gene in yeast. J. Biol. Chem. 265, 12711-12716.

KOLCH, W., HEIDECKER, G., LLOYD, P., and RAPP, U. R. (1991). Raf-1 protein kinase is required for growth of induced NIH3T3 cells. Nature 349, 426-428.

KORIOTH, F., GIEFFERS, C., and FREY, J. (1994). Cloning and characterization of the human gene encoding aspartyl beta-hydroxylase. Gene 150, 395-399.

KYRAKIS, J. M., APP, H., ZHANG, X.-F., BANERJEE, P., BRAUTIGAN, D. L., RAPP, U. R., and AVRUCH, J. (1992). Raf-1 activates MAP kinase-kinase. Nature 358, 417-421.

LAWSON, J. E., and DOUGLAS, M. G. (1988). Separate genes encode functionally equivalent ADP/ATP carrier proteins in Saccharomyces cerevisiae. Isolation and analysis of AAC2. J. Biol. Chem. 263, 14812-14818.

LIANG, P., and PARDEE, A. B. (1992). Differential display of eukaryotic mRNA by means of the polymerase chain reaction. Science 257, 967-971.

LIM, K. Y., HONG, C. S., and KIM, D. H. (2000). cDNA cloning and characterization of human cardiac junctin. Gene 255, 35-42.

LUCIAKOVA, K., HODNY, Z., BARATH, P., and NELSON, B. D. (2000). In vivo mapping of the human adenine nucleotide translocator-2 (ANT2) promoter provides support for regulation by a pair of proximal Sp-1-activating sites and an upstream silencer element. Biochem. J. 352, 519-523.

MANIATIS, T., Fritsch, E. F., and AAMBROOK, J. (1982). A Laboratory Manual. Cold Spring Harbor Laboratory Press, Cold Spring Harbor, N.Y.

MARSHALL, C. J. (1995). Specificity of receptor tyrosine kinase signaling: transient versus sustained extracellular signal-regulated kinase activation. Cell 80, 179-185.

MARZO, I., BRENNER, C., ZAMZAMI, N., SUSIN, S. A., BEUTNER, G., BRDICZKA, D., REMY, R., XIE, Z. H., REED, J. C., and KROEMER, G. (1998). The permeability transition pore complex: a target for apoptosis regulation by caspases and bcl-2-related proteins. J. Exp. Med. 187, 1261-1271.

MONIA, B., JOHNSTON, J. F., GEIGER, T., MULLER, M., and FABBRO, D. (1996). Antitumor activity of a phosphorothioate antisense oligodeoxynucleotide targeted against c-raf kinase. Nature Med. 2, 668-675.

NAKAMURA, T., RUIZ-LOZANO, P., LINDNER, V., YABE, D., TANIWAKI, M., FURUKAWA, Y., KOBUKE, K., TASHIRO, K., LU, Z., ANDON, N. L., SCHAUB, R., MATSUMORI, A., SASAYAMA, S., CHIEN, K. R., and HONJO, T. (1999). DANCE, a novel secreted RGD protein expressed in developing, atherosclcerotic, and balloon-injured arteries. J. Biol. Chem. 274, 22476-22483.

NECKELMANN, N., LI, K., WADE, R. P., SHUSTER, R., and WALLACE, D. C. (1987). cDNA sequence of a human skeletal muscle ADP/ATP translocator: lack of a leader peptide. Divergence from a fibroblast translocator cDNA, and coevolution with mitochondrial DNA genes. Proc. Natl. Acad. Sci. USA 84, 7580-7584.

PATEL, B., RAY, S., WHITESIDE, T. L. W., and KASID, U. (1997a). Constitutive activation of Raf-1 correlates with morphological transformation and abrogation of tyrosine phosphorylation of distinct sets of proteins in human squamous carcinoma cells. Mol. Carcinog. 18, 1-6.

PATEL, S., WANG, F.-H., WHITESIDE, T. L., and KASID, U. (1997b). Constitutive modulation of Raf-1 protein kinase is associated with differential gene expression of several known and unknown genes. Mol. Med. 3, 674-685.

PATEL, S., WANG, F.-H., WHITESIDE, T. L., and KASID, U. (1997c). Identification of seven differentially displayed transcripts in human primary and matched metastatic head and neck squamous carcinoma cell lines: Implications in metastasis and/or radiation response. Eur. J. Cancer B. Oral Oncol. 33, 197-203.

PFEIFER, A., MARK, G., LEUNG, S., DOUGHERTY, M., SPILLARE, E., and KASID, U. (1998). Effects of c-raf-1 and c-myc expression on radiation response in an in vitro model of human small-cell-lung-carcinoma. Biochem. Biophy. Res. Commun. 252, 481-486.

PFERIFER, A. M. A., MARK, G. E., 3., MALAN-SHIBLEY, L., GRAZLKNO, S., AMSTAD, P., and HARRIS, C. C. (1989). Cooperation of c-raf-1 and c-myc protooncogenes in the neoplastic transformation of simian virus 40 large tumor antigen-immortalized human bronchial epithelial cells. Proc. Natl. Acad. Sci. USA 86, 10075-10079.

QURESHI, S. A., RIM, M., BRUDER, J. T., KOLCH, W., RAPP, U., SUKHATME, V. P., and FOSTER D. A. (1991). An inhibitory mutant of c-Raf-1 blocks v-Src-induced activation of the Egr-1 promoter. J. Biol. Chem. 266, 20594-20597.

RAPP, U. R. (1991). Role of Raf-1 serine/threonine protein kinase in growth factor signal transduction. Oncogene 6, 495-500.

REBAY, I., FLEMING, R. J., FEHON, R. G., CHERBAS, L., CHERBAS, P., and ARTAVANIS-TSAKONAS, S. (1991). Specific EGF repeats of Notch mediate interactions with Delta and Serrate: implications for Notch as a multifunctional receptor. Cell 67, 687-699.

REES, D. J., JONES, J. M., HANDFORD, P. A., WALTER, S. J., ESNOUF, M. P., SMITH, K. J., and BROWNLEE, G. G. (1988). The role of beta-hydroxyaspartate and adjacent carboxylate residues in the first EGF domain of human factor IX. EMBO J. 7, 2053-2061.

ROGERS, G. R., MARKOVA, N. G., LAURENZI, V. D., RIZZO, W. B., and COMPTON, J. G. (1997). Genomic organization and expression of the human fatty aldehyde dehydrogenase gene (FALDH). Genomics 39, 127-135.

SHENGFENG, L. I., and SEDIVY, J. M. (1993). Raf-1 protein kinase activates the NF-κB transcription factor by dissociating the cytoplamic NFκ-IκB complex. Proc. Natl. Acad. Sci. USA 90, 9247-9251.

SOLDATENKOV, V. A., DRITSCHILO, A., WANG, F.-H., OLAH, Z., ANDERSON, W. B., and KASID, U. (1997). Inhibition of Raf-1 protein kinase by antisense phosphorothioate oligodeoxyribonucleotide is associated with sensitization of human laryngeal squamous carcinoma cells to gamma radiation. Cancer J Sci. Am. 3, 13-20.

STANTON, V. P., NICHOLS, D. W., LAUDANO, A. P., and COOPER, G. M. (1989). Definition of the human raf amino-terminal regulatory region by deletion mutagenesis. Oncogene 15, 53-61.

STENFLO, J. (1991). Structure-function relationships of epidermal growth factor modules in vitamin K-dependent clotting factors. Blood 78, 1637-1651.

SUN, B. S., ZHU, X., CLAYTON, M. M., PAN, J., and FETELSON, M. A. (1998). Identification of a protein isolated from senescent human cells that binds to hepatitis B virus X antigen. Hepatology, 27, 228-239.

SUNNERHAGEN, M. S., PERSSON, E., DAHLQVIST, I., DRAKENBERG, T., STENFLO, J., MAYHEW, M., ROBIN, M., HANDFORD, P., TILLEY, J. W., CAMPBELL, I. D., and BROWNLEE, G. G. (1993). The effect of aspartate hydroxylation on calcium binding to epidermal growth factor-like modules in coagulation factors IX and X. J. Biol. Chem. 268, 23339-2344.

SUY, S., ANDERSON, W. B., DENT, P., CHANGE, E., and KASID, U. (1997). Association of Grb2 with Sos and Ras with Raf-1 upon gamma irradiation of breast cancer cells. Oncogene 15, 53-61.

TORPPMAIR, J., CLEVELAND, J. L., ASKEW, D. S., and AGRAWAL, S. (1992). V-Raf/f-Myc synergism in abrogation of IL-3 dependence: v-Raf suppresses apoptosis. Curr. Top. Microbiol. Immunol. 182, 453-460.

WANG, H. G., RAPP, U. R., and REED, J. C. (1996). Bcl-2 targets the protein kinase Raf-1 to mitochondria. Cell 87, 629-638.

TABLE 1

Sizes of differentially displayed fragments in DU-145 cells treated with ASR versus control cells

| Differentially Displayed Fragments | Primer Combination Used | | Approximate Size of Amplified Product (bp)[c] |
|---|---|---|---|
| | Arbitrary Primer[a] | Anchor Primer[b] | |
| ASR-12a | H-AP6 | H-$T_{11}$C | 300 |
| ASR-12b | H-AP4 | H-$T_{11}$C | 300 |
| ASR-13 | H-AP6 | H-$T_{11}$C | 300 |
| ASR-17 | H-AP2 | H-$T_{11}$G | 550 |
| ASR-21 | H-AP4 | H-$T_{11}$G | 400 |
| ASR-23 | H-AP4 | H-$T_{11}$G | 250 |
| ASR-25 | H-AP4 | H-$T_{11}$G | 250 |

[a]AP2 = 5'-GATTGCC-3'; AP4 = 5'-CTCAACG-3'; AP6 = 5'-GCACCAT-3'.
[b]H = 5'-AAGCTT-3'.
[c]Size of the amplified PCR products was determined by 1.5% agarose gel electrophoresis.

TABLE 2

Identification of partial cDNA fragments

| cDNA Fragment | Fragment Sizes (bp) | DNA database (Accession No.) | Identification | Reference |
|---|---|---|---|---|
| ASR-12a | 255 | GenBank (XM_011647) | Human asprtate β-hydroxylase (BAH) | |
| ASR-12b | 229 | GenBank (NM_003146) | Human structure-specific recognition protein1 (SSRP1) | |
| ASR-13 | 247 | GenBank (XM_015283) | Human mitochondrial oxodicarboxylate carrier (OXDC) | |
| ASR-17 | 479 | GenBank (J03592) | Human ADP/ATP translocase (ANT) | |
| ASR-21 | 347 | GenBank (AF403223) | Novel (SHINC-2) | This study |
| ASR-23 | 193 | GenBank (NM_000382) | Human fatty aldehyde dehydrogenase (ALDH 10) | |
| ASR-25 | 191 | GenBank (AF403224) | Novel (SHINC-3) | This study |

TABLE 3

Densitometric scanning analysis of changes in the steady levels of gene expression

| cDNA Fragment | Transcripts Size (kb) | Changes in % |
|---|---|---|
| ASR-12a(BAH) | 5.2 | 20% |
| | 4.5 | 83% |
| | 2.8 | 14% |
| ASR-12b(SSRP1) | 2.8 | 200% |
| ASR-13(OXDC) | 4.5 | 50% |
| | 3.0 | 70% |
| | 2.0 | 109% |
| ASR-17(ANT) | 4.0 | 42% |
| | 1.3 | 96% |
| ASR-21(SHINC-2) | 6.5 | 27% |
| | 3.5 | 24% |
| | 2.5 | 81% |
| ASR-23(ALDH10) | 4.0 | 37% |
| ASR-25(SHINC-3) | 8.5 | 50% |
| | 4.0 | 71% |
| | 2.5 | 42% |

What is claimed is:

1. An isolated nucleic acid molecular comprising a polynucleotide selected from the group consisting of
   (a) a polynucleotide comprising nucleotides 1 to 2684 of SEQ ID NO: 2
   (b) a polynucleotide comprising nucleotides 2 to 2684 of SEQ ID NO: 2, and
   (c) a complete polynucleotide complement of the polynucleotide of (a) or (b).

2. The isolated nucleic acid of claim 1, which is DNA.

3. A method of making a recombinant vector comprising inserting a nucleic acid molecule of claim 1 into a vector in operable linkage to a promoter.

4. A recombinant vector produced by the method of claim 3.

5. The recombinant vector of claim 4, wherein the vector further comprises an expression cassette.

6. A method of making a recombinant host cell comprising introducing the recombinant vector of claim 4 or 5 into a host cell.

7. A recombinant host cell produced by the method of claim 6.

8. A recombinant method of producing a polypeptide, comprising culturing the recombinant host cell of claim 7 under conditions such that said polypeptide is expressed and recovering said polypeptide.

* * * * *